(12) United States Patent
Berger et al.

(10) Patent No.: US 9,101,485 B2
(45) Date of Patent: Aug. 11, 2015

(54) INTERVERTEBRAL IMPLANT WITH MULTIPLE RADII

(75) Inventors: Roger Berger, Oberdorf (CH); Rado Marjanovic, Haegendorf (CH); Joern Richter, Oberdorf (CH); David Koch, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 34 days.

(21) Appl. No.: 12/984,511

(22) Filed: Jan. 4, 2011

(65) Prior Publication Data

US 2012/0172988 A1   Jul. 5, 2012

(51) Int. Cl.
*A61F 2/44* (2006.01)
*A61F 2/30* (2006.01)

(52) U.S. Cl.
CPC ....... *A61F 2/4425* (2013.01); *A61F 2002/3065* (2013.01); *A61F 2002/30607* (2013.01); *A61F 2002/30616* (2013.01); *A61F 2002/30652* (2013.01); *A61F 2002/30654* (2013.01); *A61F 2002/30662* (2013.01); *A61F 2002/30663* (2013.01); *A61F 2002/30673* (2013.01); *A61F 2002/30682* (2013.01); *A61F 2002/30884* (2013.01); *A61F 2002/30943* (2013.01); *A61F 2002/443* (2013.01); *A61F 2310/00023* (2013.01); *A61F 2310/00029* (2013.01); *A61F 2310/00167* (2013.01); *A61F 2310/00179* (2013.01); *A61F 2310/00203* (2013.01); *A61F 2310/00239* (2013.01); *A61F 2310/00317* (2013.01)

(58) Field of Classification Search
CPC .............................................. A61F 2/44–2/447
USPC ............................................ 623/17.11–17.16
See application file for complete search history.

(56) References Cited

U.S. PATENT DOCUMENTS

| 4,759,766 | A | 7/1988 | Buettner-Janz et al. | |
|---|---|---|---|---|
| 5,401,269 | A * | 3/1995 | Buttner-Janz et al. | 623/17.15 |
| 6,682,562 | B2 * | 1/2004 | Viart et al. | 623/17.14 |
| 2004/0073311 | A1 * | 4/2004 | Ferree | 623/17.14 |
| 2004/0133278 | A1 * | 7/2004 | Marino et al. | 623/17.14 |
| 2006/0036325 | A1 * | 2/2006 | Paul et al. | 623/17.14 |
| 2006/0041314 | A1 * | 2/2006 | Millard | 623/17.16 |
| 2006/0111783 | A1 * | 5/2006 | Aflatoon et al. | 623/17.14 |
| 2006/0212122 | A1 * | 9/2006 | Perera | 623/17.14 |

(Continued)

FOREIGN PATENT DOCUMENTS

| DE | WO 2012/045340 A1 * | 4/2012 | ................ A61F 2/44 |
|---|---|---|---|
| WO | WO 02/089701 | 11/2002 | |

(Continued)

*Primary Examiner* — Eduardo C Robert
*Assistant Examiner* — Michelle C. Eckman
(74) *Attorney, Agent, or Firm* — Baker & Hostetler LLP

(57) ABSTRACT

An intervertebral implant comprises a number of components including upper and lower endplates and one or more inserts configured to be disposed between the upper and lower endplates. Complimentary curved articulation surfaces are defined on the insert-facing surfaces of the upper and lower endplates and on the corresponding upper and lower surfaces of each of the inserts. The components of the implant articulate with respect to each other along shared articulation surfaces. At least two pairs of shared articulation surfaces are defined, each pair having a different length radius. The components of the implant can be configured with retainers, such that the implant is retained in an assembled configuration when disposed within an intervertebral space.

28 Claims, 18 Drawing Sheets

(56) References Cited

U.S. PATENT DOCUMENTS

| | | |
|---|---|---|
| 2007/0299524 A1* | 12/2007 | Rivin .................... 623/17.13 |
| 2008/0234686 A1* | 9/2008 | Beaurain et al. ............. 606/90 |
| 2009/0082867 A1* | 3/2009 | Sebastian Bueno et al. .................... 623/17.16 |
| 2009/0082868 A1 | 3/2009 | Cordaro et al. |
| 2009/0138090 A1* | 5/2009 | Hurlbert et al. ......... 623/17.16 |
| 2009/0210059 A1* | 8/2009 | McCombe et al. ....... 623/17.14 |
| 2009/0326656 A1* | 12/2009 | de Villiers et al. ....... 623/17.15 |
| 2010/0030338 A1* | 2/2010 | Simon .................. 623/17.16 |
| 2010/0137992 A1* | 6/2010 | Buttner-Janz et al. ..... 623/17.16 |
| 2011/0238185 A1* | 9/2011 | Filippi et al. ............ 623/17.16 |
| 2011/0320003 A1* | 12/2011 | Duggal et al. ........... 623/17.16 |

FOREIGN PATENT DOCUMENTS

| | | | |
|---|---|---|---|
| WO | WO 2005/053580 | 6/2005 | |
| WO | WO 2006/105603 | 10/2006 | |
| WO | WO 2009149371 A1 * | 12/2009 | .......... A61F 2/44 |
| WO | WO 2010/015755 | 2/2010 | |

* cited by examiner

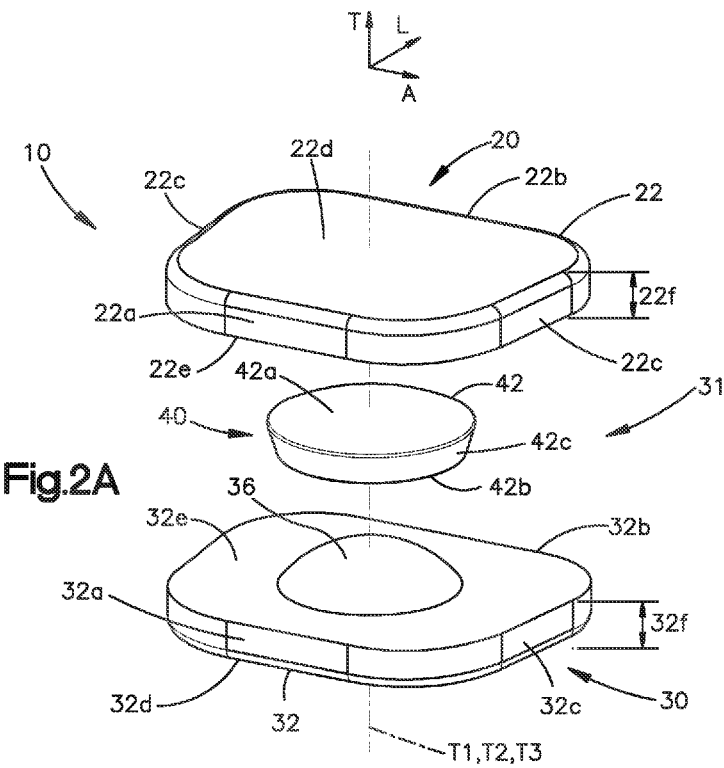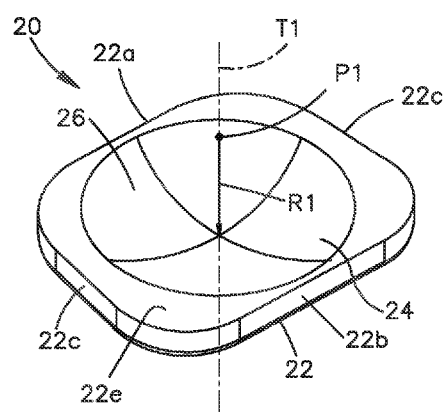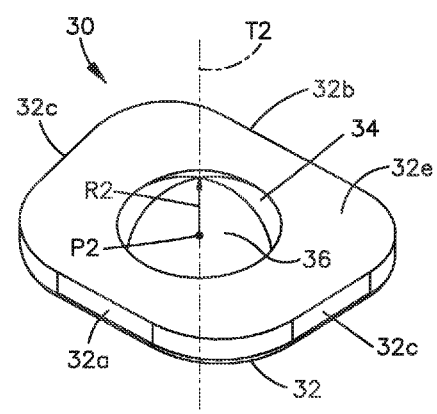

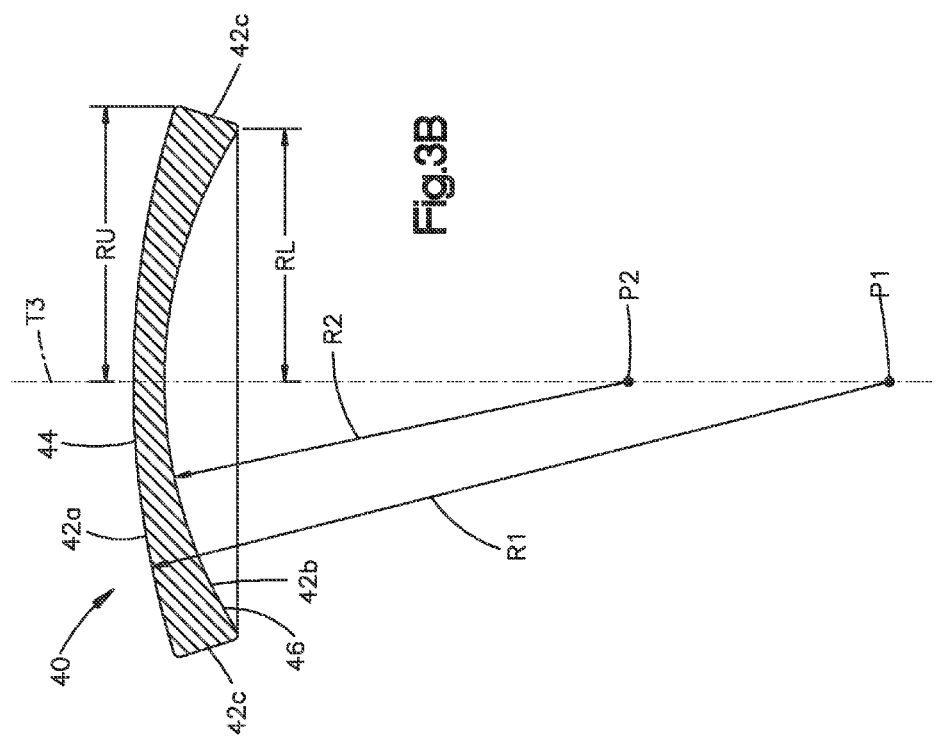
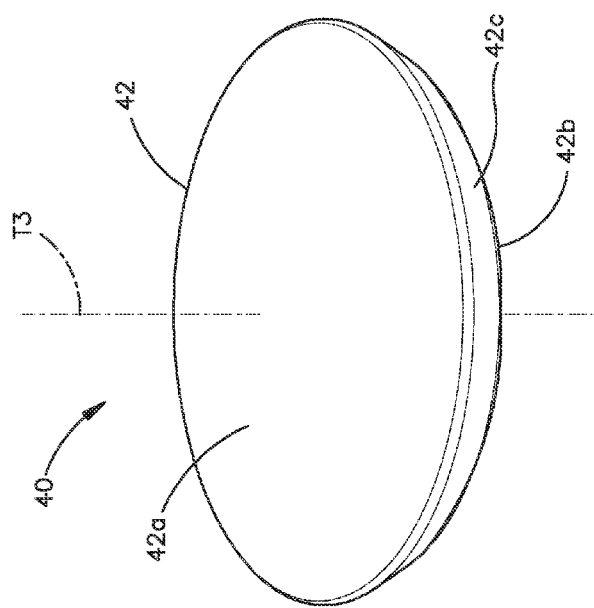

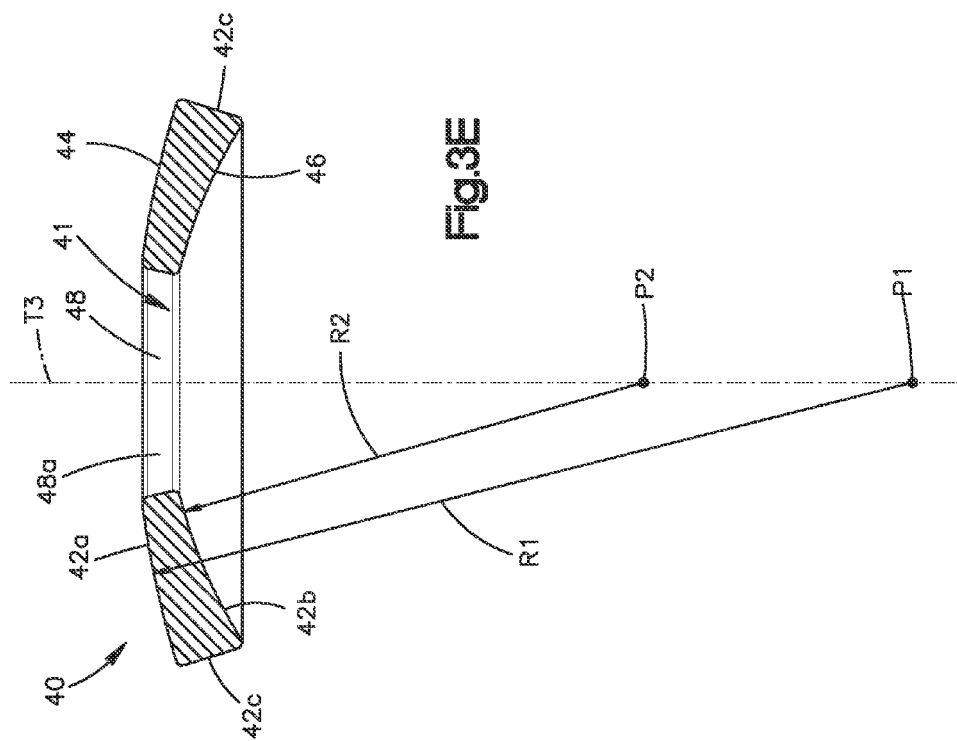
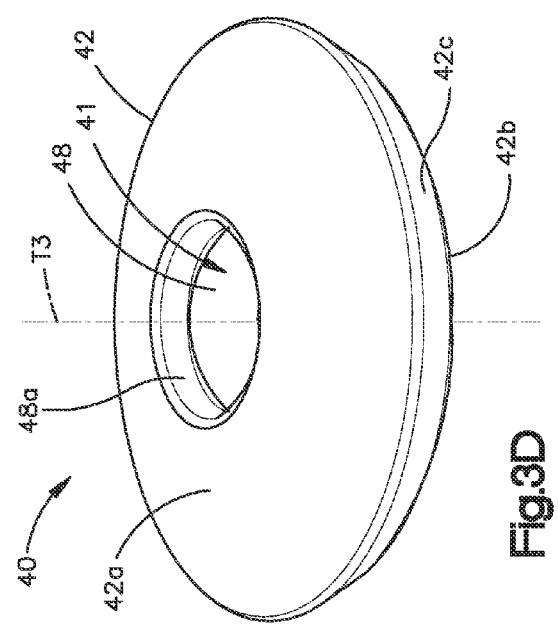

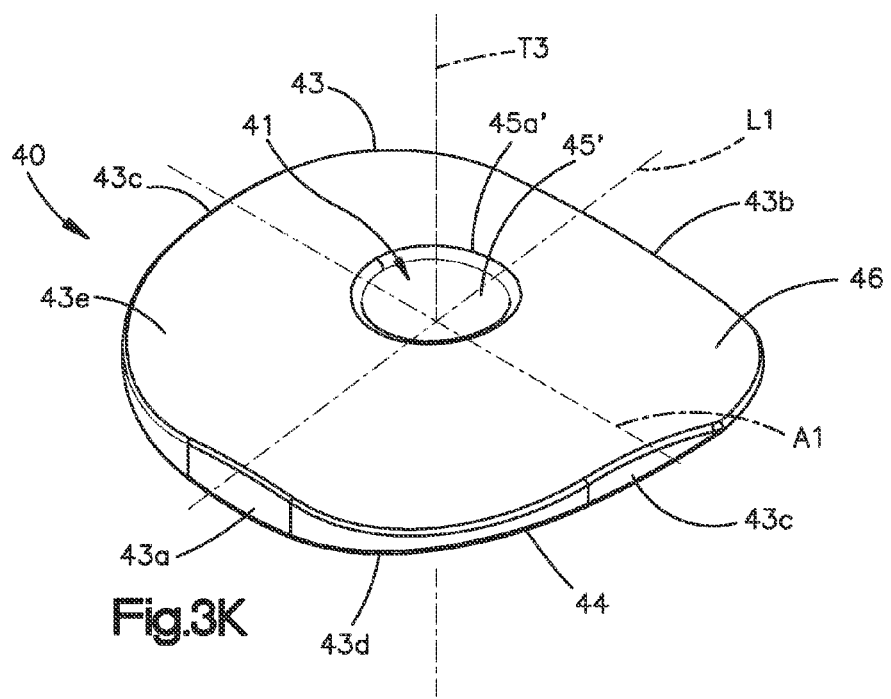

INTERVERTEBRAL IMPLANT WITH MULTIPLE RADII

BACKGROUND

Several surgical options may be employed to restore sagittal balance to a patient subsequent to a discectomy procedure. One option is to perform a total disc arthroplasty procedure, during which an artificial intervertebral disc implant is disposed into the intervertebral space left vacant by the discectomy. Typically, intervertebral disc implants are designed to maintain mobility within the operated-on motion segment.

An example of such an intervertebral disc implant includes an upper part mounted to an adjacent vertebral body and having a first curved surface, and a lower part mounted to another adjacent vertebral body and having a complimentary second curved surface with the same radius as the first curved surface. The complimentary curved surfaces allow the upper and lower parts to articulate with respect to each other. However, intervertebral disc implants that articulate along surfaces defined by a single radius require precise placement within the intervertebral space to maximize mobility. Thus, there exists a continuing need for improvements of these types of implants.

SUMMARY

In accordance with one embodiment, an implant includes upper and lower implant bodies and an insert assembly. The upper implant body has an outer bone-facing surface and an inner surface that presents a first dome-shaped surface defined by a first radius. The lower implant body has an outer bone-facing surface and an inner surface that presents a second dome-shaped surface defined by a second radius that is different in length from the first radius. The insert assembly is configured to be disposed between the upper and lower implant bodies, and includes at least one insert having an upper and lower curved surfaces that are configured to articulate along the first and second dome-shaped surfaces, respectively.

BRIEF DESCRIPTION OF THE DRAWINGS

The foregoing summary, as well as the following detailed description of the preferred embodiments of the application, will be better understood when read in conjunction with the appended drawings. For the purposes of illustrating the intervertebral implant with multiple radii, there are shown in the drawings preferred embodiments. It should be understood, however, that the instant application is not limited to the precise arrangements and/or instrumentalities illustrated in the drawings, in which:

FIG. 2A is a an exploded perspective view of the intervertebral implant illustrated in FIG. 1B, constructed in accordance with an embodiment including upper and lower endplates and an implant insert disposed between the endplates;

FIG. 2B is a perspective view of the upper endplate of the intervertebral implant illustrated in FIG. 2A;

FIG. 2C is a perspective view of the lower endplate of the intervertebral implant illustrated in FIG. 2A;

FIG. 3A is a perspective view of the implant insert of the intervertebral implant illustrated in FIG. 2A;

FIG. 3B is a sectional side elevation view of the implant insert illustrated in FIG. 3A;

FIG. 3D is a perspective view of an implant insert constructed in accordance with an alternative embodiment;

FIG. 3E is a sectional side elevation view of the implant insert illustrated in FIG. 3D;

FIG. 3K is a perspective view of the lower surface of the implant insert illustrated in FIG. 3J;

DETAILED DESCRIPTION

Figure 1B:
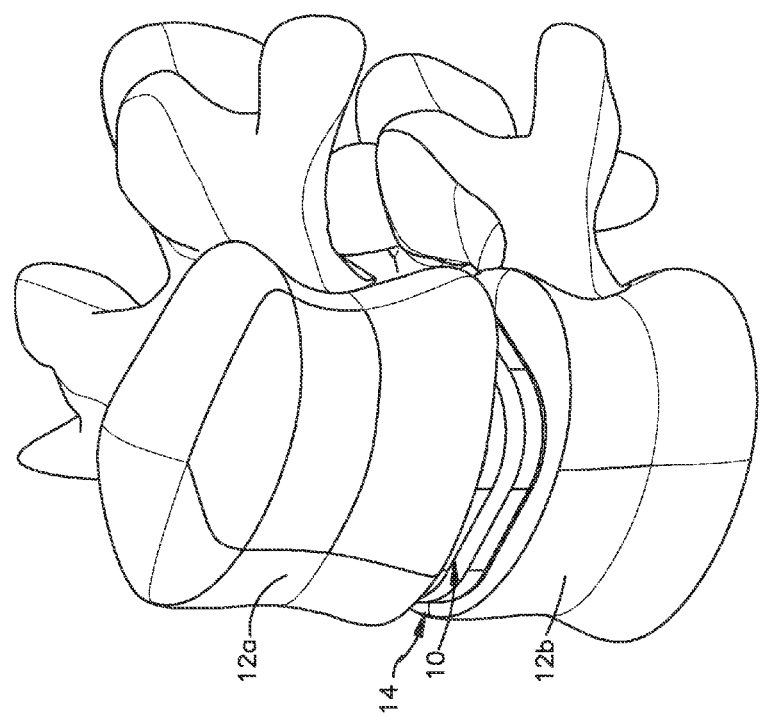
FIG. 1B is a perspective view of the vertebral bodies illustrated in FIG. 1A with an intervertebral implant with multiple radii disposed within the intervertebral space in accordance with an embodiment.

For convenience, the same or equivalent elements in the various embodiments illustrated in the drawings have been identified with the same reference numerals. Certain terminology is used in the following description for convenience only and is not limiting. The words "right", "left", "top" and "bottom" designate directions in the drawings to which reference is made. The words "inward", "inwardly", "outward", and "outwardly" refer to directions toward and away from, respectively, the geometric center of the device and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting. The words "vertebral body" as used herein should be interpreted broadly to include all the bones and bony structures found within and in the immediate proximity of the human spinal system, including but not limited to those found in the cervical region, the thoracic region, the lumbar region, and the sacral curve region. The words "float", "floating", "floatingly" and related words refer to states of engagement between the objects being referred to, wherein one or more of the objects referred to may be engaged with each other, but not fixed with respect to each other, such that one or more of the objects can move, or articulate, with respect to the others, for example via rotation, translation, and the like. The terminology intended to be non-limiting includes the above-listed words, derivatives thereof and words of similar import.

Figure 1A:
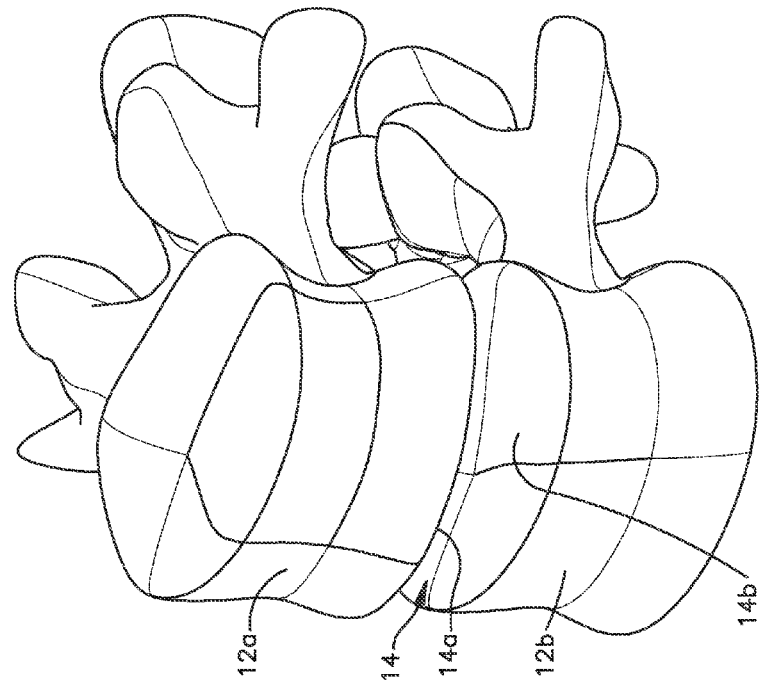
FIG. 1A is a perspective view of a pair of vertebral bodies separated by an intervertebral space.

Referring initially to FIGS. 1A-B, a superior vertebral body 12a defines a superior vertebral surface 14a of an intervertebral space 14, and an adjacent inferior vertebral body 12b defines an inferior vertebral surface 14b of the intervertebral space 14. Thus, the intervertebral space 14 is defined between the vertebral bodies 12a-b. The vertebral bodies 12a-b can be anatomically adjacent vertebral bodies, or can remain after a discectomy has been performed that removed a vertebral body from a location between the vertebral bodies 12a-b. As illustrated, the intervertebral space 14 remains after a discectomy, whereby the disc material has been removed to prepare the intervertebral space 14 to receive an orthopedic implant, such as an intervertebral implant 10 having multiple radii as illustrated in FIGS. 2A-C. The implant 10 can be disposed within the intervertebral space 14, for example to restore height within the spinal column while simultaneously maintaining mobility. The intervertebral space 14 can be located anywhere along the spine as desired.

Referring now to FIGS. 2A-C, the implant 10 generally comprises a number of components, including a first, or upper, endplate 20 configured to engage a vertebral body, such as the superior vertebral body 12a, a second, or lower endplate 30 configured to engage an adjacent vertebral body, such as the inferior vertebral body 12b, and an insert assembly 31 disposed between the endplates 20 and 30. The insert assembly 31 can include at least one implant insert 40, such as a plurality of inserts 40, configured to be floatingly disposed between the upper and lower endplates 20 and 30, respectively, such that the inserts 40 and the upper and lower endplates 20 and 30 can articulate with respect to each other about one or more contact, or articulation, surfaces. The implant 10, including the components of the implant 10, can be made from any suitable material including one or more of a variety of biocompatible, implantable grade materials, including: ceramics, composites, and/or ceramic matrix composites such as aluminum oxide, zirconia toughened alumina (ZTA), silicon nitride, polycrystalline diamond, and the like; hardened and/or hardened coated metals, such as titanium alloy, diamond-like carbon (DLC), cobalt chrome, and the like; polymers such as ultra-high-molecular-weight polyethylene (UHMWPE), and the like; or any other suitable material as desired. Of course the components of the implant 10 can all be made of a single material, or the components can be made of any combination of a variety of materials, as desired.

The upper endplate 20 includes a first, or upper, endplate body 22 defining a distal, or posterior end 22a, an opposing proximal, or anterior end 22b, and opposed sides 22c extending between the distal and proximal ends 22a-b, respectively. The endplate body 22 further includes an upper, or outer, bone-facing surface 22d and an opposing lower, or inner, implant-facing surface 22e. The upper surface 22d can be may be smooth, may have gripping features such as teeth, spikes, keels, or similar structures formed thereon and configured to facilitate gripping engagement between the upper surface 22d and adjacent structure, such as the end plate of an adjacent vertebral body, or may have any number of discrete smooth and gripping portions formed thereon. The upper surface 22d may define a flat, or generally flat, planar surface, or may be defined to conform to the anatomy of adjacent structure, such as the end plate of an adjacent vertebral body. The lower surface 22e may define a flat, or generally flat, planar surface, and may be configured with one or more contact, or articulation surfaces, as described in more detail below.

Similarly, the lower endplate 30 includes a first, or lower, endplate body 32 defining a distal, or posterior end 32a, an opposing proximal, or anterior end 32b, and opposed sides 32c extending between the distal and proximal ends 32a and 32b, respectively. The endplate body 32 further includes a lower, or outer, bone-facing surface 32d and an opposing upper, or inner, implant-facing surface 32e. The lower surface 32d can be may be smooth, may have gripping features such as teeth, spikes, keels, or similar structures formed thereon and configured to facilitate gripping engagement between the lower surface 32d and adjacent structure, such as the end plate of an adjacent vertebral body, or may have any number of discrete smooth and gripping portions formed thereon. The lower surface 32d may define a flat, or generally flat, planar surface, or may be formed to conform to the anatomy of adjacent structure, such as the end plate of an adjacent vertebral body. The upper surface 32e may define a flat, or generally flat, planar surface, and may be configured with one or more contact, or articulation surfaces, as described in more detail below.

The sides of each endplate 20 and 30 are spaced apart from each other along a lateral direction A. The anterior ends and corresponding posterior ends of each endplate 20 and 30 are spaced apart from each other along a longitudinal direction L that is angularly offset (e.g., perpendicular) with respect to the lateral direction A. The bone-facing surface and implant-facing surface of each of the endplates 20 and 30 are spaced from each other along a transverse direction T that is angularly offset (e.g., perpendicular) with respect to both the lateral direction A and the longitudinal direction L. When the implant 10 is in a neutral orientation such that the endplates 20 and 30 are substantially parallel to each other, the lateral direction A extends generally in a medial-lateral direction, the longitudinal direction L extends generally in an anterior-posterior direction, and the transverse direction T extends generally in a cranial-caudal direction. Thus, reference can be made herein to the directional components of the implant 10 as illustrated in the neutral orientation, it being appreciated that the actual orientation of the endplates 20 and 30 are configured to change during use.

The upper endplate defines a transverse thickness 22f of the upper endplate 20 as defined between the upper and lower surfaces 22d and 22e. The transverse thickness 22f may be uniform throughout the body 22, as illustrated in FIGS. 2A-B, or may vary, for example between the distal and proximal ends 22a and 22b and/or between the sides 22c. In an alternative embodiment, the thickness 22f may vary between the distal and proximal ends 22a and 22b, for example the thickness 22f may be greater at the proximal end 22b than at the distal end 22a. For example, the thickness 22f may taper, or increase, gradually from the distal end 22a to the proximal end 22b. Of course the thickness 22f of the upper end plate 20 may be varied according to any other configuration as desired.

The lower endplate 30 defines a transverse thickness 32f as defined between the lower and upper surfaces 32d and 32e. The transverse thickness 32f may be uniform throughout the body 32, as illustrated in FIGS. 2A and 2C, or may vary, for example between the distal and proximal ends 32a and 32b and/or between the sides 32c. In an alternative embodiment, the thickness 32f may vary between the distal and proximal ends 32a and 32b, for example the thickness 32f may be greater at the proximal end 32b than at the distal end 32a. For example, the thickness 32f may taper, or increase, gradually from the distal end 32a to the proximal end 32b. Of course the thickness 32f of the lower end plate 30 may be varied according to any other configuration as desired.

The upper endplate 20 defines a recess 24 that extends into the lower surface 22e of the body 22. The recess 24 is configured to accept an insert 40 in floating engagement therein. The recess 24 defines a contact, or articulation, surface 26 within the body 22 that is configured to floatingly engage with a complimentary articulation surface of an insert 40. The articulation surface 26 can be curved, and for instance can be dome-shaped as desired. For example, as illustrated in FIG. 2B, the articulation surface 26 has a concave, spherical shape, as defined by a portion of a sphere, the sphere defined by a first radius R1 extending in an upward, or cranial, direction from an inferior first articulation point P1. The articulation point P1 can be defined within an adjacent, inferior, vertebral body, as described in more detail below, when the implant 10 is disposed in the intervertebral space 14. The recess 24 can be centered on a first transverse axis T1 that extends centrally through the upper endplate 20. That is, the transverse axis T1 can be located equidistantly between the distal and proximal ends 22a and 22b, and can be located equidistantly between the sides 22c. The diameter and depth of the recess 24 with respect to the lower surface 22e are determined by the location of the articulation point P1, and the length of the first radius R1. For example, the first articulation point P1 and the first radius R1 may be selected such that at least a portion of the lower surface 22e remains outside the circumference of the recess 24, as depicted in FIG. 2B. Alternatively, the first articulation point P1 and the first radius R1 may be selected such that the recess 24 comprises the entirety of the lower surface 22e of the body 22. Thus, it should be appreciated that the first articulation point P1 and the first radius R1 can be selected as desired to at least partially determine the size and shape of the recess 24.

It should be noted that although the recess 24 is illustrated in FIG. 2B as a concave spherical recess that is centered in the lower surface 22e of the body 22 of the upper endplate 20, the recess 24 can be defined using any alternative geometry and/or at any other location within the lower surface 22e as desired. Further, it should be noted that the upper endplate 20 is not limited to having a single recess 24, and that multiple recesses of identical or varying geometry may be defined at various locations within the lower surface 22e of the body 22.

The lower endplate 30 defines a raised projection 34 that extends outward from the upper surface 32e of the body. The projection 34 is configured to be floatingly disposed adjacent to an insert 40. The projection 34 defines a contact, or articulation, surface 36 that is configured to floatingly engage with a complimentary articulation surface of an insert 40. The articulation surface 36 can be curved, and for instance can be dome-shaped as desired. For example, as illustrated in FIG. 2C, the articulation surface 36 has a convex, spherical shape, as defined by a portion of a sphere, the sphere defined by a second radius R2 extending in an upward, or cranial, direction from an inferior second articulation point P2. The second articulation point P2 can be defined within an adjacent, inferior, vertebral body, as described in more detail below, when the implant 10 is disposed in the intervertebral space 14. The first and second radii R1 and R2 of the recess 24 and the projection 34, respectively, generally are of different lengths. As illustrated in FIGS. 2B-C, the length of R1 is greater than the length of R2. In alternative embodiments, the length of R2 may be greater than the length of R1, or the lengths of R1 and R2 may be equal. The difference in lengths between R1 and R2 enables a range of articulations of the components of the implant 10 with respect to each other, as described in more detail below.

The projection 34 can be centered on a second transverse axis T2 that extends centrally through the lower endplate 30. That is, the second transverse axis T2 can be located equidistantly between the distal and proximal ends 32a and 32b, and can be located equidistantly between the sides 32c. The diameter and height of the projection 34 with respect to the upper surface 32e are determined by the location of the second articulation point P2, and the length of the second radius R2. For example, the second articulation point P2 and the second radius R2 may be selected such that at least a portion of the upper surface 32e remains outside the circumference of the projection 34, as depicted in FIG. 2C. Alternatively, the second articulation point P2 and the second radius R2 may be selected such that the projection 34 comprises the entirety of the upper surface 32e of the body 32. Thus, it should be appreciated that the second articulation point P2 and the second radius R2 can be selected as desired to at least partially determine the size and shape of the projection 34.

It should be noted that although the projection 34 is illustrated in FIG. 2C as a convex, spherical projection that is centered on the upper surface 32e of the body 32 of the lower endplate 30, the projection 34 can be defined using any alternative geometry and/or at any other location on the upper surface 32e as desired. Further, it should be noted that the lower endplate 30 is not limited to having a single projection 34, and that multiple projections of identical or varying geometry may be defined at various locations on the upper surface 32e of the body 32. Furthermore, while in the instant figures and description the upper endplate 20 defines the recess 24 and the lower endplate 30 defines the projection 34, it should be appreciated that either or both of the endplates can define a recess and/or projection as described herein with reference to the recess 24 and the projection 34.

Referring generally to FIGS. 3A-J, the insert assembly 31 can include one or more inserts 40 defined in a variety of configurations as desired. For example, referring to FIGS. 3A-C, the insert 40 defines a generally round, disc shaped insert body 42 that arcs radially outward from a transverse axis T3 between a convex upper surface 42a and a transversely opposed concave lower surfaces 42b, terminating at a circumferential peripheral surface, or side, 42c. The upper and lower surfaces 42a and 42b can define respective diameters that are centered on the transverse axis T3. The diameters, or cross-sectional dimensions, of the upper and lower surfaces 42a and 42b can be equal, or can be of differing lengths. It should be appreciated that while substantially circular structures are described herein as defining respective diameters, they can be alternatively shaped, and thus define cross-sectional dimensions. Thus, a structure that defines a diameter can also define any suitable alternatively shaped cross-sectional dimension unless otherwise indicated.

As illustrated, peripheral surface 42c is beveled radially inward along the inferior direction, so as to define an angle with respect to the transverse axis T3. Accordingly, the diameter of the upper surface 42a, as defined by an upper radius RU, is greater than the diameter of the lower surface 42b, as defined by a lower radius RL. All or a portion of the upper and lower surfaces 42a and 42b can be configured as contact, or articulation surfaces 44 and 46, respectively. Each of the articulation surfaces 44 and 46 are configured to floatingly engage with a complimentary articulation surface of a respective endplate body, such as the articulation surface 26 of the upper endplate body 20, or the articulation surface of another component of the implant 10, such as a second insert 40.

The upper and lower surfaces 42a and 42b are curved. Preferably, the respective curvatures of the upper and lower surfaces 42a and 42b are of differing geometric profiles. As illustrated, the insert 40 is configured to be disposed in floating engagement between the upper and lower endplates 20 and 30 of the implant 10, respectively. Specifically, the upper surface 42a of the insert 40 has a convex, spherical shape, as defined by a portion of a sphere having a radius equal to, or substantially equal to, the length of the first radius R1 extending upward from the first articulation point P1. The lower surface 42b of the insert 40 has a concave, spherical shape, as defined by a portion of a sphere having radius equal to, or substantially equal to, the length of the second radius R2 extending upward from the second articulation point P2. The curvatures of the upper and lower surfaces 42a and 42b allows contact along common, or shared, articulation surfaces of the components, for example between the articulation surface 26 of the upper end plate 20 and the articulation surface 44 of the insert 40, and between the articulation surface 36 of the lower end plate 30 and the articulation surface 46 of the insert 40 when the insert 40 is disposed between the endplates of the implant 10, as depicted in FIG. 2A. The curvature of the upper surface 42a of the insert 40 can be defined such that a portion, up to a substantial entirety of the articulation surface 44 is placed into contact with the complimentary articulation surface 26 defined by the recess 24 when the insert 40 is disposed within the implant 10. Similarly, the curvature of the lower surface 42b of the insert 40 can be defined such that a portion, up to a substantial entirety of the articulation surface 46 is placed into contact with the complimentary articulation surface 36 defined by the projection 34 when the insert 40 is disposed within the implant 10. In accordance with one embodiment, a substantial entirety of respective pairs of lines extending along the curved upper and lower surfaces 42a and 42b between ends at opposing sides of the insert 40, the lines intersecting at the respective apices of the curved upper and lower surfaces 42a and 42b, respectively, can be in substantially continuous contact with complementary articulation surfaces defined by adjacent components of the implant 10, for instance as may be defined by inner surfaces 22e and 32e of the upper and lower endplates 20 and 30 respectively, when the insert 40 is disposed within the implant 10. Thus, it should be appreciated that surface contact along the complimentary articulation surfaces can be maintained during articulation of the components of the implant 10 with respect to each other.

Figure 3C:
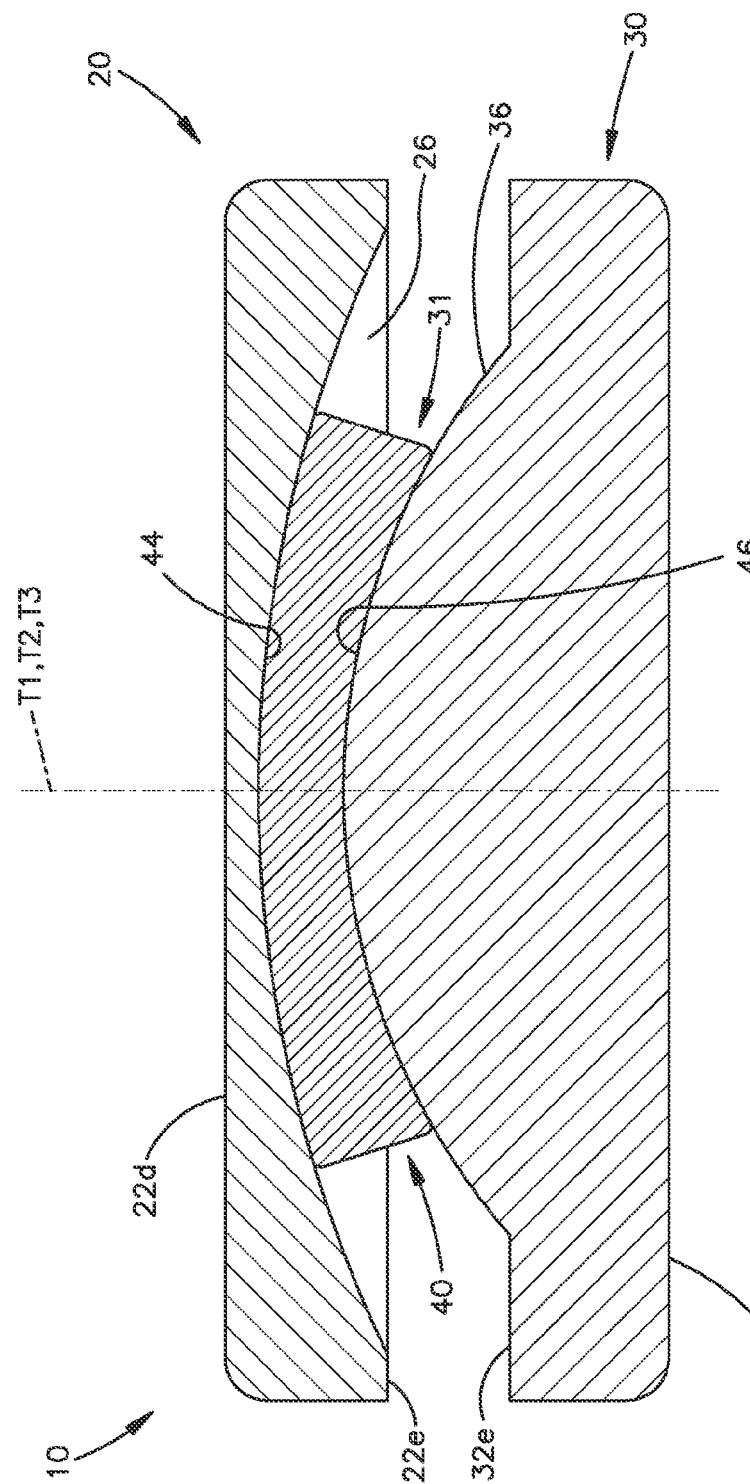
FIG. 3C is a sectional side elevation view of the intervertebral implant illustrated in FIG. 2A.

In an example configuration illustrated in FIG. 3C, the insert 40 is floatingly disposed between the upper and lower endplates 20 and 30, respectively, of the implant 10. The upper endplate 20 is capable of articulation with respect to the insert 40, along the common articulation surfaces 26 and 44, independently of whether the insert 40 articulates concurrently with the bottom endplate 30, along the shared, or common, articulation surfaces 36 and 46. Similarly, the insert 40 is capable of articulation with respect to the bottom endplate 30, along the shared, or common, articulation surfaces 36 and 46, independently of whether the upper endplate 20 articulates concurrently with the insert 40, along the common articulation surfaces 26 and 44. Of course, the upper and lower endplates 20 and 30, and the insert 40 are capable of concurrently articulating with respect to each other along the respective shared articulation surfaces. Thus, one of the endplates 20 and 30 can articulate relative to the insert 40 alone or in combination with articulation of the other of the endplates 20 and 30 relative to the insert 40. It should be appreciated that the articulation surfaces of one or more, up to all of the components of the implant 10, such as the endplates 20 and 30 and the insert 40, can be defined such that contact between adjacent components of the implant 10 along any of the respective shared, or common articulation surfaces, such as the articulation surfaces 36 and 46, and/or 26 and 44, is maintained throughout one or more portions of, up to the full range of articulation of the adjacent components with respect to each other. Maintaining surface contact along the articulation surfaces may reduce wear on the components of the implant 10.

In an alternative embodiment, depicted in FIGS. 3D-E, the insert body 42 may define a retainer 41, such as the aperture 48 extending transversely through the body 42 from the upper surface 42a through the lower surface 42b, for instance along the transverse axis T3. Alternatively, the aperture 48 may extend only partially into the upper surface 42a, may extend only partially into the lower surface 42b, or a pair of apertures could be defined, extending into each of the upper and lower surfaces 42a-b, respectively. The aperture 48 can have a circular cross section, and define a diameter or cross-sectional dimension less than that of each of the upper and lower surfaces 42a and 42b, respectively. The size of the aperture 48 can determine the surface area of the articulation surfaces 44 and 46, which in turn can impact the articulation characteristics of the insert 40 with respect to the other components of the implant 10. The aperture 48 can be configured to receive a complimentary retainer 41 defined on an adjacent component of the implant 10, such as pin 25 (See FIGS. 4C-I). When received in the aperture 48, the pin 25 can act to retain the insert 40 within the implant, as described in more detail below. Additionally, the diameter of the aperture 48 can be defined such that it operates in unison with the complimentary retainer to limit articulation, or motion, of the implant 10. For example, the insert 40 and other components of the implant 10, such as the endplates 20 and 30 and any additional inserts of the implant 10, have a range of articulation that is limited by engagement between the circumferential inner surface 48a of the aperture 48 and the complimentary retainer. It should be appreciated that the geometry of the aperture 48 is not limited to the illustrated cylindrically shaped aperture geometry, and that the aperture 48 can alternatively be configured with any suitable aperture geometry.

Figure 3F:
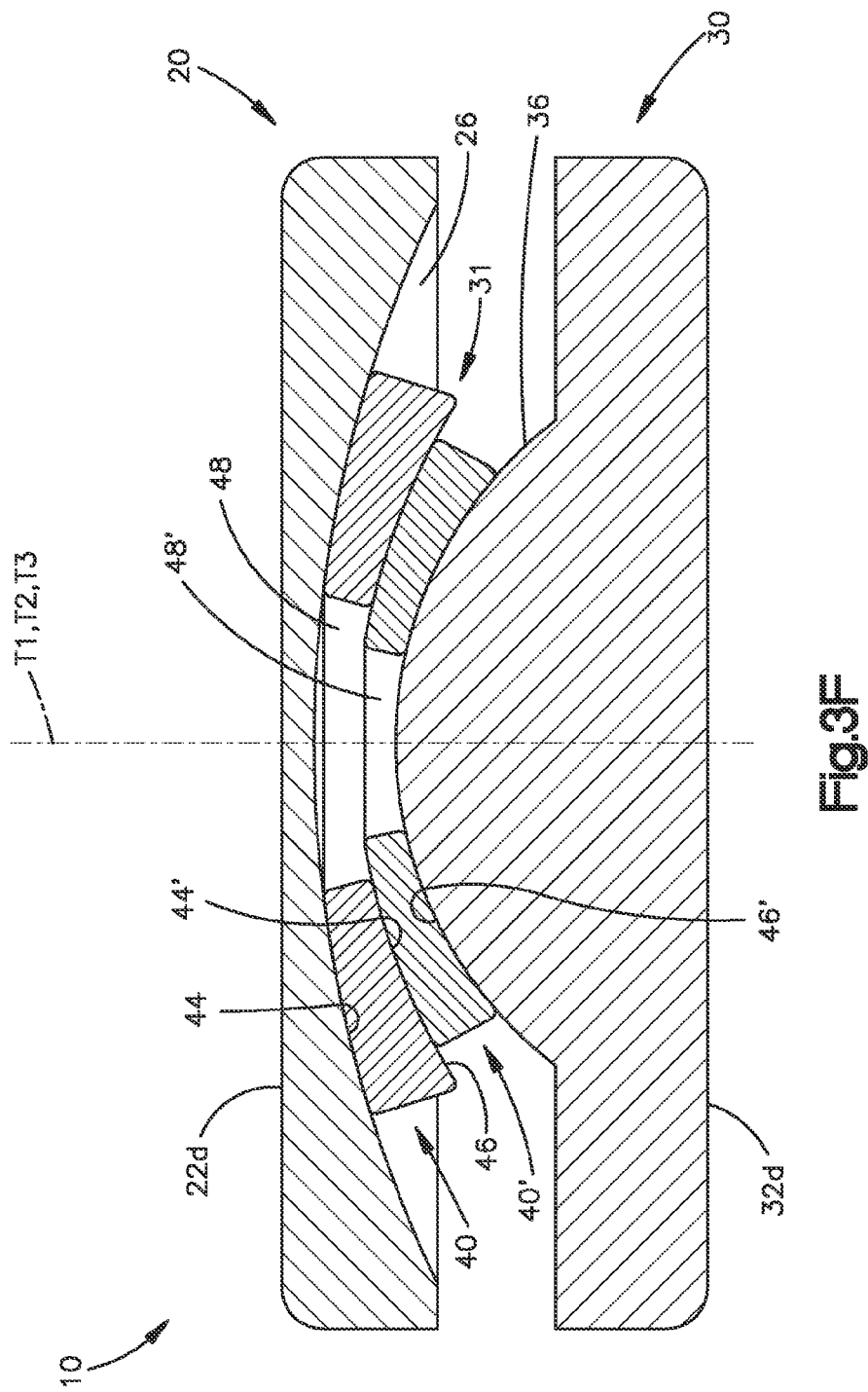
FIG. 3F is a sectional side elevation view of an intervertebral implant constructed in accordance with an alternative embodiment, including upper and lower endplates and a pair of implant inserts as illustrated in FIG. 3D disposed between the endplates.

Referring now to FIG. 3F, the insert assembly 31 can include more than one insert 40, for instance if it is desired to construct the implant 10 including additional articulation surfaces, thereby enhancing the overall resolution of the articulation of the implant 10 (i.e., allowing for finer degrees of articulation among the components of the implant 10). For example, the insert assembly 31 of the illustrated embodiment includes first and second inserts 40 and 40', respectively, having respective articulation surfaces 44 and 46, and 44' and 46', and apertures 48 and 48'. The diameters, or cross-sectional dimensions of the apertures 48 and 48' can be sized the same or differently. For example, the diameters of the apertures 48 and 48' can be sized in accordance with a desired amount of contact surface between the first and second inserts 40 and 40', and between the first and second inserts 40 and 40' and surrounding components of the implant 10, thereby allowing fine adjustment of the floating resistance between the first and second inserts 40 and 40' and/or surrounding components of the implant 10. Furthermore, if the first and second inserts 40 and 40' and/or the surrounding components of the implant 10 are constructed of different materials, it may be desirable to size the diameters of the first and second inserts 40 and 40' in order to control stress levels within the first and second inserts 40 and 40' and/or the surrounding components of the implant 10 during articulation, or motion, of the implant 10.

The inserts 40 and 40' are floatingly disposed adjacent to each other, between the upper and lower endplates 20 and 30, respectively, of the implant 10. Any two of the components of the implant 10 are capable of articulation with respect to each other, independent of articulation between any of the remaining components. For example, the upper endplate 20 is capable of articulation with respect to the insert 40, along the common articulation surfaces 26 and 44, independently of whether the insert 40 articulates concurrently with the insert 40', along the shared, or common, articulation surfaces 46 and 44', or whether the insert 40' articulates concurrently with the bottom endplate 30, along the shared, or common, articulation surfaces 46' and 36. Of course, any number of, or all of, the upper and lower endplates 20 and 30, and the inserts 40 and 40', are capable of concurrently articulating with respect to each other along the respective shared articulation surfaces.

Figure 3H:
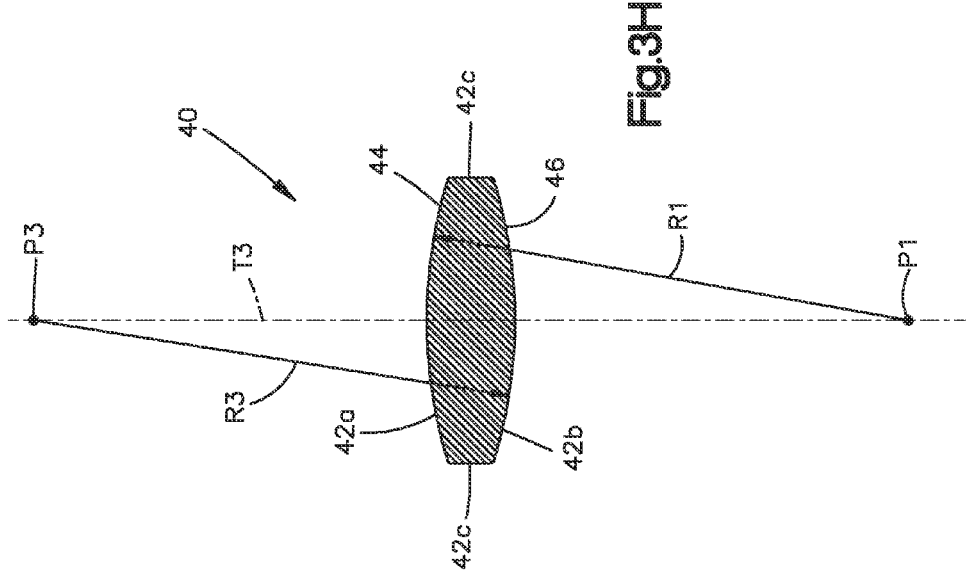
FIG. 3H is a sectional side elevation view of the implant insert illustrated in FIG. 3G.
Figure 3G:
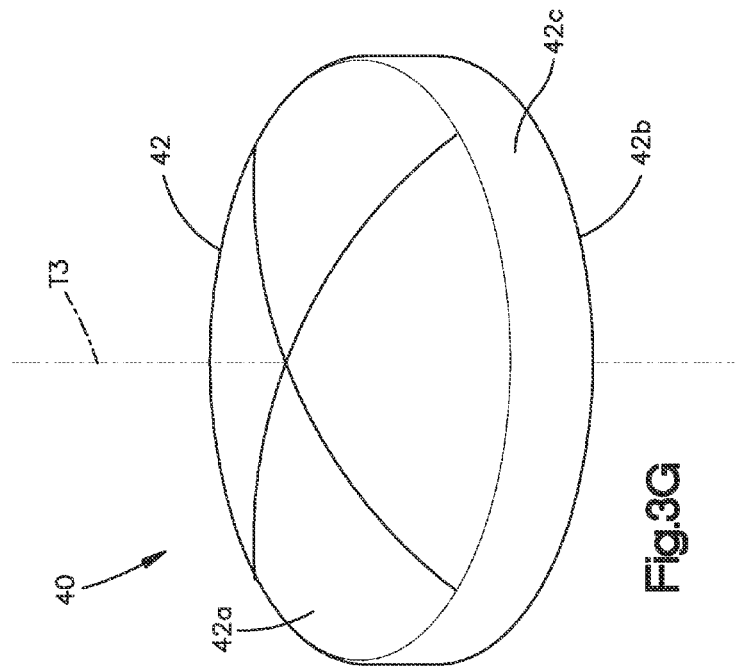
FIG. 3G is a perspective view of an implant insert in accordance with another alternative embodiment.
Figure 3I:
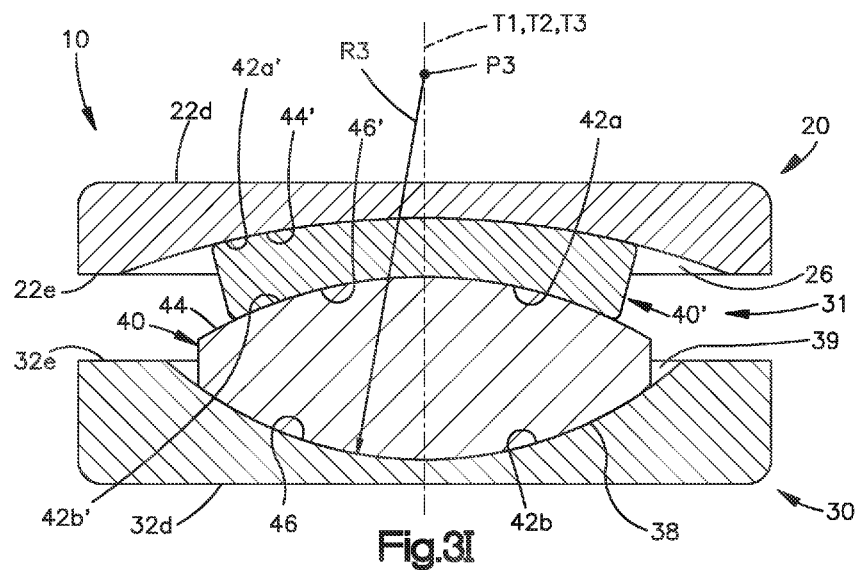
FIG. 3I is a sectional side elevation view of an intervertebral implant constructed in accordance with an alternative embodiment, including upper and lower endplates, and the implant inserts illustrated in FIGS. 3A and 3G disposed between the endplates.

It should be appreciated that, although the upper and lower surfaces 42a and 42b, and thus the articulation surfaces 44 and 46, respectively, have been described and illustrated thus far with matching directions of curvature, the upper and lower surfaces 42a and 42b, and thus the articulation surfaces 44 and 46 can have different directions of curvature. For instance, as illustrated in FIGS. 3G-I, the upper and lower surfaces 42a and 42b can have opposing directions of curvature. As depicted, the upper surface 42a of the insert 40 can be substantially dome-shaped, and thus can have a convex, substantially spherical shape, as defined by a portion of a sphere having a radius extending in an upward, or cranial, direction from an inferior articulation point, such as the first radius R1 extending upward from the first articulation point P1, or the like. The lower surface 42b of the insert 40 can be substantially dome-shaped, and thus can have a convex, substantially spherical shape, as defined by a portion of a sphere having a third radius R3 extending in a downward, or caudal, direction from a superior third articulation point P3. The third articulation point P3 can be selected so as to be disposed within an adjacent, superior, vertebral body, as described in more detail below, when the implant 10 is disposed in the intervertebral space 14.

As depicted in FIG. 3I, the lower endplate 30 can define a recess 38 that extends into the upper surface 32e of the endplate body 32. The recess 38 can be configured to accept the bottom surface 42b of the insert 40 so that the insert 40 is in floating engagement with the lower endplate 30. The recess 38 defines a contact, or articulation, surface 39 within the upper surface 32e of the body 32 that is configured to floatingly engage with the complimentary articulation surface 46 of the insert 40. The recess 38 can be dome-shaped, and thus can have a concave, substantially spherical shape, as defined by a portion of a sphere, the sphere having a radius equal to, or substantially equal to, the length of the third radius R3 that extends down from the superior articulation point P3. The diameter and depth of the recess 38 with respect to the upper surface 32e are defined by the desired location of the articulation point P3, and the length of the third radius R3. For example, the articulation point P3 and the radius R3 may be selected such that at least a portion of the upper surface 32e remains outside the circumference of the recess 38. Alternatively, the articulation point P3 and the radius R3 may be selected such that the recess 38 comprises the entirety of the upper surface 32e of the body 32. The length of the radius R3 may be lesser than, equal to, or greater than the length of the radius R1, depending upon the desired articulation characteristics of the resulting articulation surfaces.

Referring to FIG. 3I, the insert assembly 31 can be constructed of first and second implants 40 and 40'. The first insert 40 can be constructed with opposed curved convex upper and lower surfaces 42a and 42b, respectively. The second insert 40' can be constructed with convex upper surface 42a' and opposing concave lower surface 42b'. The inserts 40 and 40' are floatingly disposed with respect to each other and with respect to the complementary lower and upper endplates 30 and 20, respectively, of the implant 10. The curvatures of the upper and lower surfaces 42a and 42b of the insert 40 and of the upper and lower surfaces 42a' and 42b' of the insert 40' allows contact along common, or shared, articulation surfaces of the components, for example between the articulation surface 26 of the upper end plate 20 and the articulation surface 44' of the insert 40', between the articulation surface 46' of the insert 40' and the articulation surface 44 of the insert 40, and between the articulation surface 39 of the lower end plate 30 and the articulation surface 46 of the insert 40, when the inserts 40' and 40 are disposed between the endplates of the implant 10, as depicted in FIG. 3I.

The curvature of the upper surface 42a' of the insert 40' can be defined such that a portion, up to a substantial entirety of the articulation surface 44' is placed into contact with the complimentary articulation surface 26 defined by the recess 24 when the insert assembly 31 is disposed within the implant 10. Similarly, the curvature of the lower surface 42b of the insert 40 can be defined such that a portion, up to a substantial entirety of the articulation surface 46 is placed into contact with the complimentary articulation surface 39 defined by the recess 38 when the insert assembly 31 is disposed within the implant 10. As illustrated, the curvatures of the lower surface 42b' of the insert 40' and the upper surface 44 of the insert 40 can be defined such that a portion, up to a substantial entirety of the articulation surface 46' is placed into contact with the complimentary articulation surface 44 when the inserts 40' and 40 are assembled into the insert assembly 31 and disposed within the implant 10. Of course, the insert assembly 31 can be alternatively constructed, for example with an insert 40' having a larger cross sectional dimension than the insert 40, in which case the curvatures of the lower surface 42b' of the insert 40' and the upper surface 44 of the insert 40 can be defined such that the a portion, up to a substantial entirety of the articulation surface 44 is placed into contact with the complimentary articulation surface 46' when the inserts 40' and 40 are assembled into the insert assembly 31 and disposed within the implant 10. In accordance with one embodiment, a substantial entirety of respective pairs of lines extending along the curved upper and lower surfaces 42a' and 42b' between ends at opposing sides of the insert 40', the lines intersecting at the respective apices of the curved upper and lower surfaces 42a' and 42b', respectively, can be in substantially continuous contact with complementary articulation surfaces defined by adjacent components of the implant 10, for instance as may be defined by inner surfaces 22e and 32e of the upper and lower endplates 20 and 30 respectively, when the insert 40' is disposed within the implant 10. Thus, it should be appreciated that surface contact along the complimentary articulation surfaces can be maintained during articulation of the components of the implant 10 with respect to each other.

Any two of the components of the implant 10, that is the endplates 20 and 30 and at least one insert of the insert assembly 31, are capable of articulation with respect to each other, independent of articulation between any of the remaining components. For example, the first insert 40 is capable of articulation with respect to the lower endplate 30, along the common articulation surfaces 46 and 39, independent of concurrent articulation between the inserts 40 and 40' along the shared, or common, articulation surfaces 46' and 44, and further independent of concurrent articulation between the insert 40' and the upper endplate 20, along the shared, or common, articulation surfaces 44' and 26. In other words, the upper endplate 20, the insert 40', and the insert 40, may articulate in unison, that is, remain in a static position with respect to each other, as the insert 40 articulates with respect to the lower endplate 30 along the shared articulation surfaces 46 and 39. Furthermore, the second insert 40' is capable of articulation with respect to the upper endplate 20, along the common articulation surfaces 44' and 26, independent of concurrent articulation between the inserts 40' and 40 along the shared, or common, articulation surfaces 46' and 44, and further independent of concurrent articulation between the insert 40 and the lower endplate 30, along the shared, or common, articulation surfaces 46 and 39. In other words, the lower endplate 30, the insert 40, and the insert 40', may articulate in unison, that is, remain in a static position with respect to each other, as the insert 40' articulates with respect to the upper endplate 20 along the shared articulation surfaces 44' and 26. Of course, any number of, or all of, the components of the implant 10, such as the upper and lower endplates 20 and 30, and the inserts 40 and 40', are capable of concurrently articulating with respect to each other along their respective shared articulation surfaces. It should be appreciated that the articulation surfaces of one or more, up to all of the components of the implant 10, such as the endplates 20 and 30 and the inserts 40 and 40', can be defined such that contact between adjacent components of the implant 10 along any of the respective shared, or common articulation surfaces, such as the articulation surfaces 46 and 39, 46' and 44, and/or 44' and 26, is maintained throughout one or more portions of, up to the full range of articulation of the adjacent components with respect to each other. Maintaining surface contact along the articulation surfaces may reduce wear on the components of the implant 10.

Figure 3J:
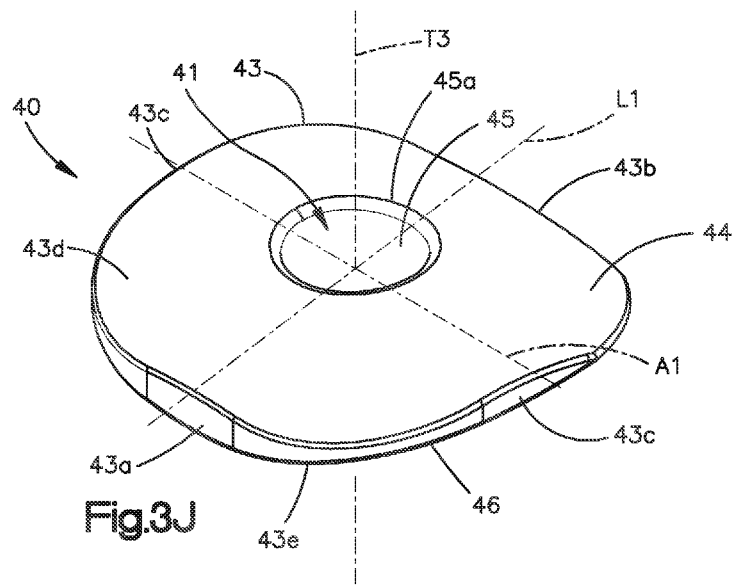
FIG. 3J is a perspective view of the upper surface of an implant insert constructed in accordance with another alternative embodiment.

Referring now to FIGS. 3J-K, while the articulation surfaces defined by the recesses 24 and 38 and/or the projections 34 of the upper and lower endplates 20 and 30, respectively, and the articulation surfaces of the implant inserts 40, have been described and illustrated herein as curved surfaces defined by a single radius, and in particular as surfaces of spherical geometry, it should be appreciated that the articulation surfaces 26, 36, 44, 46, and so on can be defined by any alternative surface geometry to promote a desired range of articulation between the components of the implant 10. For example, as illustrated, the implant insert 40 can have a generally D-shaped body 43, defined between an anterior end 43a and a longitudinally opposed posterior end 43b, and laterally opposed sides 43c. The implant body 43 can define transversely opposed upper and lower surfaces 43d and 43e that define the upper and lower articulation surfaces 44 and 46, respectively. The upper and lower surfaces 43d and 43e, respectively, are curved, and each of the upper and lower surfaces can be defined by a plurality of radii of varying lengths (i.e., multiple, or compound, radii). For instance, as will now be described, the upper and lower surfaces 43d and 43e are illustrated as double-curve surfaces, that is that each of the upper and lower surfaces 43d and 43e are defined by two distinct but coincident curved surfaces, which together define their respective surfaces.

In the illustrated embodiment, the upper surface 43d is defined by coincident first and second curved surfaces. The first curved surface extends along a longitudinal axis L1 defined through the body 43 between the anterior and the posterior ends 43a-b, respectively, the first curved surface having a substantially elliptical, half-barrel shape. The second curved surface extends along a lateral axis A1 defined through the body 43 between the laterally opposed sides 43c, respectively, the second curved surface also having a substantially elliptical, half-barrel shape, with a curvature that is different from that of the first surface. Thus, the axes L1 and A1 can be normal to each other with respect to the body 43 of the insert 40, and the coincidence of the first and second curved surfaces defines the upper surface 43d. The resulting double-curve surface can be curved, and for instance can be dome-shaped as desired.

The upper surface 43d may define a retainer 41, such as the aperture 45 extending downward into the body 43 and radially outward from the transverse axis T3. Alternatively, the aperture 45 can extend transversely through the insert body 43 from the upper surface 43d through the lower surface 43e, for instance along the transverse axis T3. The aperture 45 can be configured to receive a complimentary retainer defined on an adjacent component of the implant 10, such as pin 25 (See FIGS. 4B-C). When received in the aperture 45, the pin 25 can act to retain the insert 40 within the implant, as described in more detail below. The diameter of the recess 45 can be defined such that the aperture 45 operates in unison with the complimentary retainer to limit articulation, or motion, of the implant 10. For example, the insert 40 and other components of the implant 10, such as the endplates 20 and 30 and any additional inserts of the implant 10, have a range of articulation that is limited by engagement between the circumferential inner surface 45a of the aperture 45 and the complimentary retainer. It should be appreciated that the geometry of the aperture 45 is not limited to the illustrated cylindrically shaped aperture geometry, and that the aperture 45 can alternatively be configured with any suitable aperture geometry.

The lower surface 43e is similarly formed as a double-curve surface As illustrated, lower surface 43e is defined by coincident third and fourth curved surfaces. The third curved surface extends along the longitudinal axis L1 between the anterior and posterior ends 43a-b, respectively, the third curved surface having a substantially elliptical, half-barrel shape. The fourth curved surface extends along the lateral axis A1 between the laterally opposed sides 43c, respectively, the second curved surface also having a substantially elliptical, half-barrel shape, with a curvature that is different from that of the first surface. The third and fourth curved surfaces can be defined as opposing matches of, or differently from, the corresponding first and second curved surfaces that define the upper surface 43d. The resulting double-curve surface can be curved, and for instance can be dome-shaped as desired. Of course, the lower surface 43e can also be formed using any other geometry, such as the spherical curved surfaces described above and illustrated in FIGS. 3A-I, or the lower surface 43e can be defined as a double-curve surface while the upper surface 43d is defined by a spherical curved surface. Although the upper and lower surfaces 43d and 43e are illustrated in FIG. 3J as generally convex with respect to the body 43, it should be appreciated that one or both of the upper and lower surfaces 43d and 43e could also be defined as concave with respect to the body 43.

The lower surface 43e can also define a retainer 41, such as the aperture 45' extending upward into the body 43 and radially outward from the transverse axis T3. The aperture 45' can be configured to receive a complimentary retainer defined on an adjacent component of the implant 10, as described in more detail below. The diameter of the aperture 45' can be of lesser, equal, or greater length than the diameter of the aperture 45, for example in accordance with a desired range of articulation with an adjacent component of the implant 10, and can be defined such that the aperture 45' operates in unison with the complimentary retainer to limit articulation, or motion, of the implant 10. For example, the insert 40 and other components of the implant 10, such as the endplates 20 and 30 and any additional inserts of the implant 10, have a range of articulation that is limited by engagement between the circumferential inner surface 45a' of the aperture 45' and the complimentary retainer. It should be appreciated that the geometry of the aperture 45' is not limited to the illustrated cylindrically shaped aperture geometry, and that the aperture 45' can alternatively be configured with any suitable aperture geometry.

Of course, the adjacent surfaces of the components of the implant 10 between which the implant insert 40 depicted in FIGS. 3J-K will be disposed, for example the inner surfaces 22e and 32e of the upper and lower endplates 20 and 30 respectively, can be similarly configured with double-curve surfaces of the same, or substantially the same surface geometry, so as to facilitate a desired level of contact along the common, or shared, articulation surfaces. For example, the curvatures of the upper and lower surfaces 43d and 43e, respectively, can be defined such that a portion, up to a substantial entirety of the articulation surfaces 44 and/or 46 are placed into contact with complimentary articulation surfaces defined by adjacent components of the implant 10, for instance as may be defined by inner surfaces 22e and 32e of the upper and lower endplates 20 and 30 respectively, when the insert 40 is disposed within the implant 10. In accordance with one embodiment, a substantial entirety of respective pairs of lines extending along the curved upper and lower surfaces 43d and 43e between ends at opposing sides of the insert 40, the lines intersecting at the respective apices of the curved upper and lower surfaces 43d and 43e, respectively, can be in substantially continuous contact with complementary articulation surfaces defined by adjacent components of the implant 10, for instance as may be defined by inner surfaces 22e and 32e of the upper and lower endplates 20 and 30 respectively, when the insert 40 is disposed within the implant 10. Thus, it should be appreciated that surface contact along the complimentary articulation surfaces can be maintained during articulation of the components of the implant 10 with respect to each other.

It should be appreciated that the upper and/or lower surfaces 43d and 43e can be defined by more than two distinct curved surfaces, or by a single curved surface of multiple radii extending radially outward from the transverse axis A3 and circumferentially around the body 43 of the insert 40. Thus, the upper and lower surfaces 43d and 43e can define any combination of curved geometries as desired, such as ellipsoids, ovoids, toroids, astroids, deltoids, and the like. It should further be appreciated that the upper and lower surfaces 43d and 43e can be defined by any surface geometry suitable to promote a desired range of articulation between particular components of the intervertebral implant 10 along common, or shared, articulation surfaces.

Referring now to FIGS. 4A-I, the components of the intervertebral implant 10 can define retainers 41 configured to maintain the implant 10 in an assembled configuration within the intervertebral space 14, in particular when the adjacent vertebral bodies 12a-b move with respect to each other, for example during spinal flexion or extension, during lateral bending, twisting, and the like. In an example embodiment depicted in FIG. 4A, a retainer 41 in the form of a rim 28 is defined in the upper endplate 20, the rim 28 extending circumferentially along an inner rim surface 29 between the articulation surface 26 and the lower surface 22e of the upper endplate 20. The rim 28 can be configured to retain the insert 40 within the recess 24, for example when the peripheral surface 42c engages with the inner rim surface 29. The rim 28 can terminate at the lower surface 22e of the body 22, as depicted, or can extend beyond the lower surface 22e, defining a raised rim (not shown). The inner rim surface 29 can be defined at an angle equal to, or substantially equal to, the angle defined between the plane of the peripheral surface 42c of the insert 40 and the transverse axis T3. In addition to retaining the insert 40 within the assembled intervertebral implant 10, the rim 28 can operate to limit articulation, or motion, of the implant 10. For example, the insert 40 has a range of articulation that is limited by engagement between the peripheral surface 42c of the insert 40 and the inner rim surface 29.

Figure 4A:
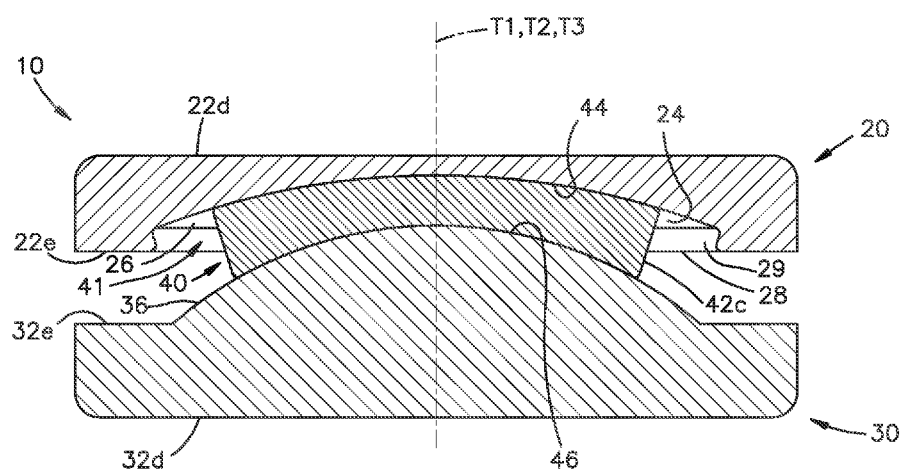
FIG. 4A is a sectional side elevation view of the intervertebral implant illustrated in FIG. 3C, wherein the upper endplate includes a retainer rim.
Figure 4B:
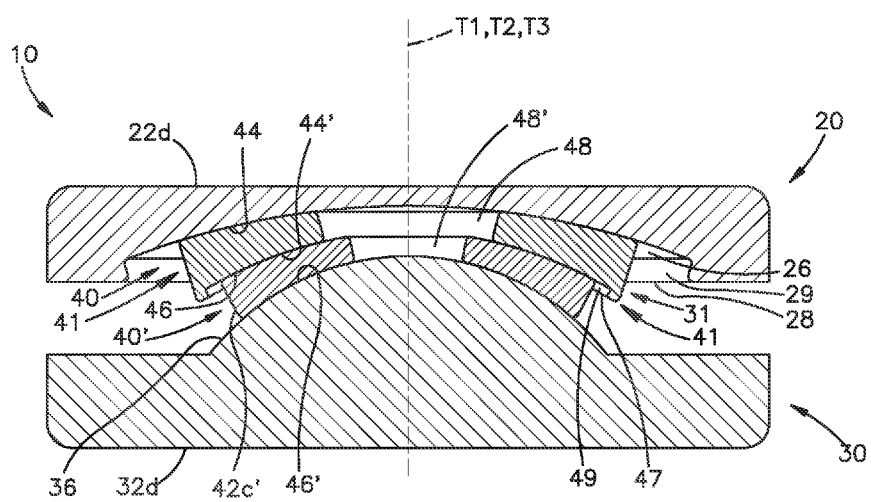
FIG. 4B is a sectional side elevation view of the intervertebral implant illustrated in FIG. 3F, wherein the upper endplate and one of the inserts include retainer rims.

Referring now to FIG. 4B depicting an alternative embodiment, the insert assembly 31 includes first and second inserts 40 and 40', respectively, having respective articulation surfaces 44 and 46, and 44' and 46', and apertures 48 and 48'. As described above, the diameters, or cross-sectional dimensions of the apertures 48 and 48' can be sized the same or differently. The implant 10 of the illustrated embodiment includes two retainers 41, the first in the form of a rim 28 defined in the upper endplate 20 as described above, the second in the form of a rim 47 extending outwardly from the articulation surface 46 of the first insert 40, the rim 47 defining a circumferential inner rim surface 49. The rim 47 can be configured to retain the second insert 40' within the articulation surface 46 of the first insert 40, for example when the peripheral surface 42c' of the second insert 40' engages with the inner rim surface 49. The inner rim surface 49 can be defined at an angle equal to, or substantially equal to, the angle defined between the plane of the peripheral surface 42c' of the second insert 40' and the transverse axis T3. In addition to retaining the second insert 40' within the assembled intervertebral implant 10, the rim 47 can operate to limit articulation, or motion, of the implant 10. For example, the second insert 40' has a range of articulation that is limited by engagement between the peripheral surface 42c' of the second insert 40' and the inner rim surface 49. Of course the rim 28 can be configured to retain the insert 40 within the recess 24 of the upper endplate 20, as described above.

Figure 4C:
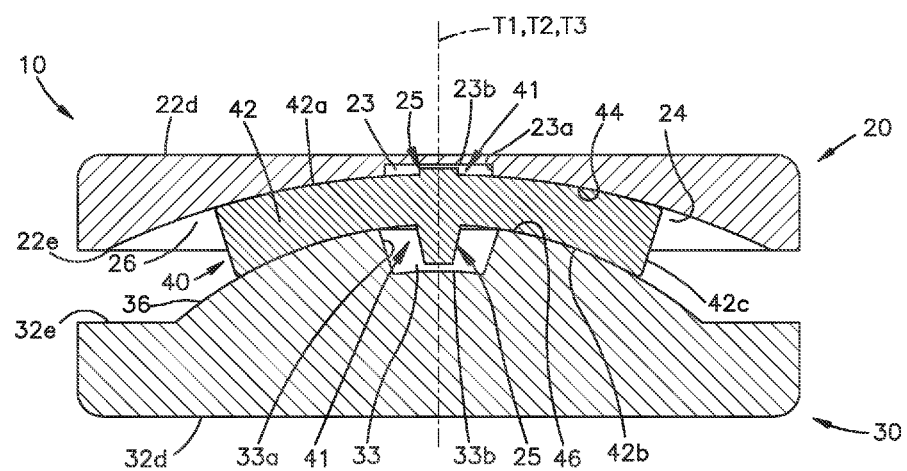
FIG. 4C is a sectional side elevation view of the intervertebral implant illustrated in FIG. 3C, wherein the upper and lower endplates include retainer apertures and the insert includes retainer pins.
Figure 4D:
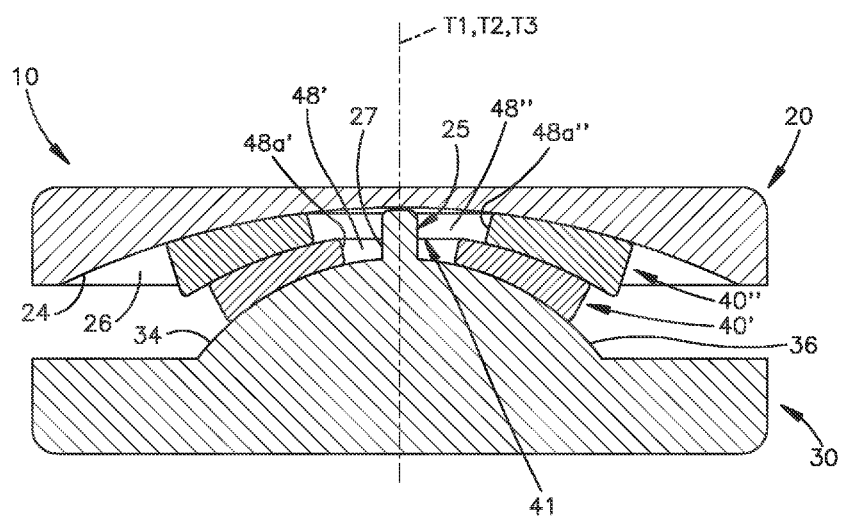
FIG. 4D is a sectional side elevation view of the intervertebral implant illustrated in FIG. 3F, in which the lower endplate includes a retainer pin and the inserts include retainer apertures.

Referring now to FIG. 4C, another alternative embodiment is illustrated, in which the upper and lower endplates 20 and 30 have retainers 41 defined therein in the form of apertures 23 and 33, respectively. The aperture 23 extends upwardly into the recess 24 of the upper endplate 20 and radially outward from the transverse axis T1. The aperture 33 extends downwardly into the projection 34 of the lower endplate 30 and radially outward from the transverse axis T3. It should be appreciated that the geometry of the apertures 23 and 33 are not limited to the illustrated cylindrically shaped aperture geometries, and that the apertures 23 and/or 33 can alternatively be configured with any suitable aperture geometries. The respective depths of the apertures 23 and 33 are configured to receive complimentary retainers 41, such as the pins 25 defined on the insert 40, therein.

The pin 25 can be defined by respective pin bodies 27 that extend outwardly from the upper and lower surfaces 42a and 42b of the body 42 of the insert 40, respectively, for instance in a transverse direction along the transverse axis T3. It should be appreciated that although the pin bodies 27 are illustrated herein as having generally cylindrical shapes, that the pins 25 can alternatively be provided with any suitable pin body 27 geometries. The pins 25 can have any suitable lengths in the transverse direction such that they extend into the respective retainers 41 they compliment, such as the apertures 23 and 33, but do not contact the bottom surfaces 23b and 33b of the apertures 23 and 33. The pins 25 can have diameters that are less than the diameters of the respective apertures 23 and 33 in which they are received. The pins 25 can operate in unison with the apertures 23 and 33 to retain the implant 10 in an assembled configuration. For example, when the pins 25 are received in the apertures 23 and 33 of the upper and lower endplates 20 and 30, respectively, the insert 40 is prevented from becoming dislodged from the implant 10 due to engagement between the inner surfaces 23a and 33a of the respective apertures 23 and 33 and the bodies 27 of the respective pins 25. The pins 25 can further operate to limit the articulation, or motion between the insert 40 and the upper and lower endplates 20 and 30. For example, articulation is prevented when the inner surfaces 23a and/or 33a of the respective apertures 23 and 33 engage the bodies 27 of the respective pins 25. It should be appreciated that the diameters, or cross-sectional dimensions of the apertures 23 and 33 can be sized the same or differently.

Referring generally to FIGS. 4D-I, further alternative embodiments of the implant 10 are illustrated in which one or more of the components of the implant 10 define one or more retainers 41, such as pins 25, and in which one or more of the components of the implant 10, such as the upper or lower endplates 20 and 30 and/or one or more, up to all, of the inserts of the insert assembly 31 define complimentary retainers 41 in the form of apertures that can operate in unison with the pins 25 to retain the intervertebral implant 10 in an assembled configuration. In particular, referring now to FIG. 4D, when the pin 25 extending upwardly from the projection 34 of the lower endplate 30 is received in the apertures 48' and 48" of the inserts 40' and 40", respectively, the inserts 40' and 40" are prevented from becoming dislodged from the implant 10 due to engagement between the inner surfaces 48a' and 48a" of the respective apertures 48' and 48" and the body 27 of the pin 25. The pin 25 can have any suitable length in the transverse direction such that it extends into the respective retainers 41 it compliments, such as the apertures 48' and 48", but does not contact the articulation surface 26 of the upper endplate 20. The pin 25 can have a diameter that is less than that of the apertures 48' and 48" of the respective inserts 40' and 40" in which it is received. The pin 25 can further operate to limit the articulation, or motion between the inserts 40' and 40" and the upper and lower endplates 20 and 30. For example, articulation is prevented when the inner surfaces 48a' and/or 48a" of the respective apertures 48' and 48" engage the body 27 of the pin 25. It should be appreciated that the diameters, or cross-sectional dimensions of the apertures 48' and 48" can be sized the same or differently.

Figure 4E:
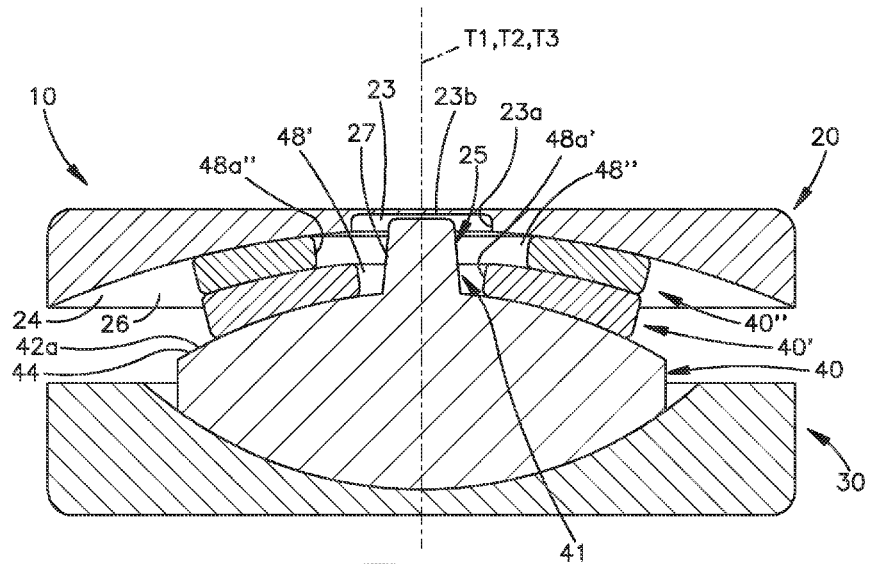
FIG. 4E is a sectional side elevation view of the intervertebral implant illustrated in FIG. 3I constructed in accordance with an alternative embodiment, in which the upper endplate includes a retainer aperture, the lowermost insert includes a retainer pin, and the remaining inserts include retainer apertures.
Figure 4F:
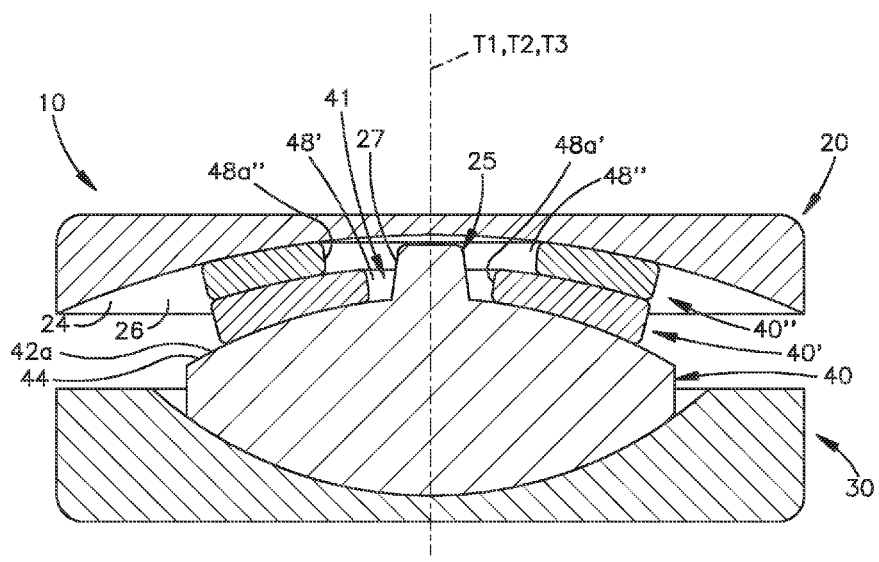
FIG. 4F is a sectional side elevation view of the intervertebral implant illustrated in FIG. 3I constructed in accordance with another alternative embodiment, in which the lowermost insert includes a retainer pin, and the remaining inserts include retainer apertures.

Referring now to FIG. 4E, when the pin 25 extending upwardly from the upper surface 42a of the insert 40 is inserted through the apertures 48' and 48" of the inserts 40' and 40", respectively, and received in the aperture 23 defined in the upper endplate 20, the inserts 40' and 40" are prevented from becoming dislodged from the implant 10 due to engagement between the inner surfaces 48a' and 48a" of the respective apertures 48' and 48" and the body 27 of the pin 25. The pin 25 can have any suitable length in the transverse direction such that it extends through the respective retainers 41 it compliments, such as the apertures 48' and 48", and is received in the aperture 23, but does not contact the bottom surface 23b of the aperture 23. Alternatively, the aperture 23 can be omitted from the upper endplate 20 and the pin 25 can have any suitable length in the transverse direction such that it extends into the respective retainers 41 it compliments, such as the apertures 48' and 48", but does not contact the articulation surface 26 of the upper endplate 20 (see FIG. 4F). The pin 25 can have a diameter that is less than the diameters of the respective apertures 48' and 48" in which it is received. The pin 25 of the illustrated embodiment defines a tapered diameter that decreases in length as the pin 25 extends outwardly from the upper surface 42a of the insert 40. Of course the pin 25 can alternatively be provided with a tapered diameter that decreases in length as the pin 25 extends outwardly from the upper surface 42a of the insert 40, a diameter that increases, decreases, or is stepped (e.g., having two or more sections, each section having a different diameter) through distinct portions of the body 27 in any combination, or a body 27 with a uniform diameter. The pin 25 can further operate to limit the articulation, or motion between the inserts 40, 40', and 40" and the upper and lower endplates 20 and 30. For example, articulation is prevented when the inner surface 23a of the aperture 23 and/or the inner surfaces 48a' and/or 48a" of the respective apertures 48' and 48" engage the body 27 of the pin 25. It should be appreciated that the diameters, or cross-sectional dimensions of the aperture 23 and the apertures 48' and 48" can be sized the same or differently.

Figure 4G:
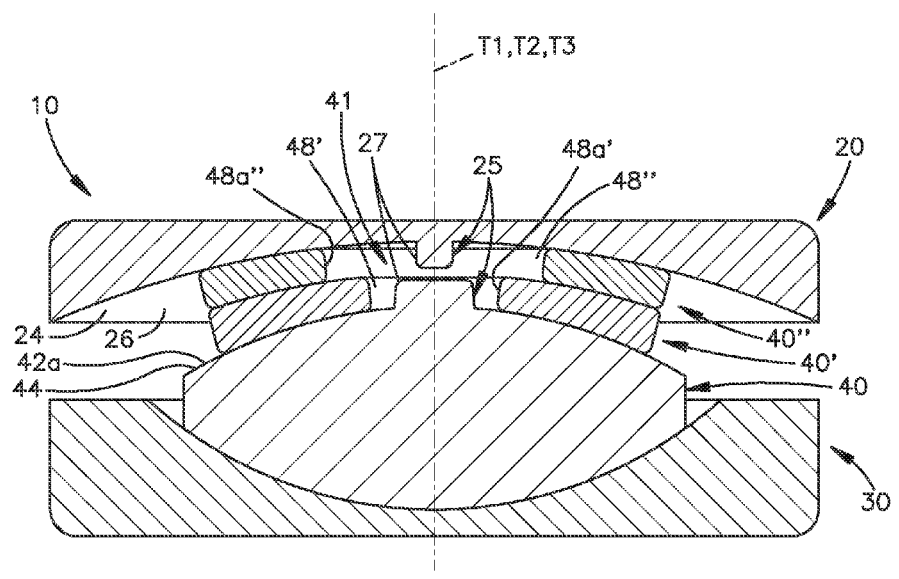
FIG. 4G is a sectional side elevation view of the intervertebral implant illustrated in FIG. 3I constructed in accordance with another alternative embodiment, in which the upper endplate and lowermost insert include retainer pins and the remaining inserts include retainer apertures.

Referring now to FIG. 4G, when the pin 25 extending upwardly from the upper surface 42a of the body 42 of the insert 40 and the pin 25 extending downwardly from the recess 24 of the upper endplate 20 are received in the apertures 48' and 48" of the inserts 40' and 40", respectively, the inserts 40' and 40" are prevented from becoming dislodged from the implant 10 due to engagement between the inner surfaces 48a' and 48a" of the apertures 48' and 48" and the bodies 27 of the respective pins 25. The pins 25 can have any suitable lengths in the transverse direction such that they extend into the respective retainers 41 they compliment, such as the apertures 48' and 48", but do not contact each other. The pins 25 can have diameters that are less than the diameters of the respective apertures 48' and 48" in which they are received. The pins 25 can further operate to limit the articulation, or motion between the inserts 40, 40', and 40" and the upper and lower endplates 20 and 30. For example, articulation is prevented when the inner surface 48a' of the aperture 48' of the insert 40' engages the body 27 of the pin 25 extending upwardly from the upper surface 42a of the insert 40, and/or when the inner surface 48a" of the aperture 48" of the insert 40" engages the body 27 of the pin 25 extending downwardly from the recess 24 of the upper endplate 20. It should be appreciated that the diameters, or cross-sectional dimensions of the apertures 48' and 48" can be sized the same or differently.

Figure 4H:
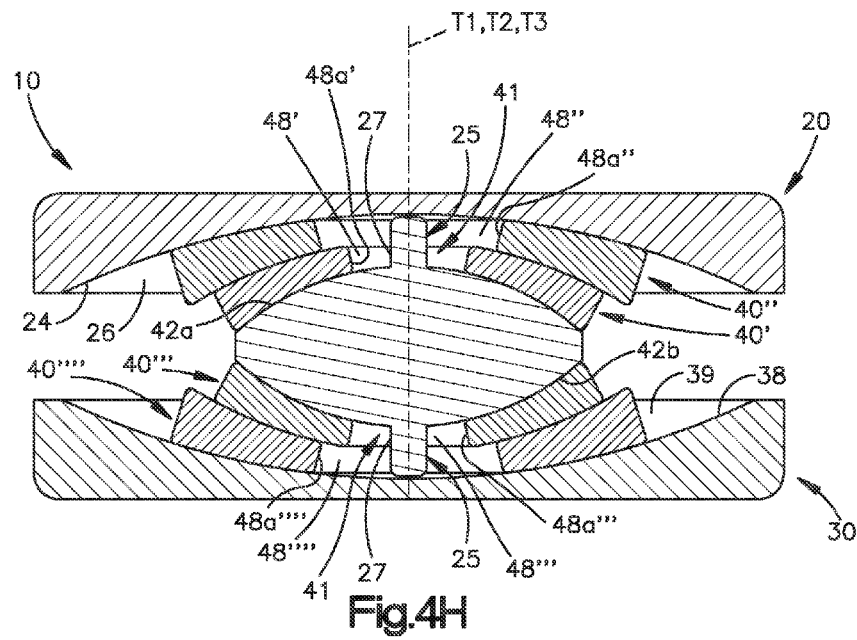
FIG. 4H is a sectional side elevation view of the intervertebral implant illustrated in FIG. 4D constructed in accordance with an alternative embodiment, in which the upper and lower endplates include retainer pins and the inserts include retainer apertures.

Referring now to FIG. 4H, when the first pin 25 extending upwardly from the upper surface 42a of the body 42 of the insert 40 is received in the apertures 48' and 48" of the inserts 40' and 40", the inserts 40' and 40" are prevented from becoming dislodged from the implant 10 due to engagement between the inner surfaces 48a' and 48a" of the apertures 48' and 48" and the body 27 of the first pin 25. Similarly, when the second pin 25 extending downwardly from the lower surface 42b of the body 42 of the insert 40 is received in the apertures 48''' and 48'''' of the inserts 40''' and 40'''', the inserts 40''' and 40' are prevented from becoming dislodged from the implant 10 due to engagement between the inner surfaces 48a''' and 48a' of the apertures 48''' and 48'''' and the body 27 of the second pin 25. The first and second pins 25 can have any suitable lengths in the transverse direction such that the first and second pins 25 extend into the respective retainers 41 they compliment, such as the apertures 48' and 48", and 48''' and 48''', respectively, but do not contact the articulation surfaces 26 and 39 of the upper and lower endplate 20 and 30. The pins 25 can have diameters that are less than the diameters of the respective apertures 48', 48", 48''', and 48'''' in which they are received. The pins 25 can further operate to limit the articulation, or motion between the inserts 40, 40', 40", 40''', and 40'''' and the upper and lower endplates 20 and 30. For example, articulation is prevented when the inner surface 48a' and 48a" of the aperture 48' and 48" of the inserts 40' and 40" engage the body 27 of the pin 25 extending upwardly from the upper surface 42a of the insert 40, and/or when the inner surface 48a''' and 48a'''' of the aperture 48''' and 48' of the inserts 40''' and 40'''' engage the body 27 of the pin 25 extending downwardly from the lower surface 42b of the insert 40. It should be appreciated that the diameters, or cross-sectional dimensions of the apertures 48', 48", 48''', and 48'''' can be sized the same or differently.

Figure 4I:
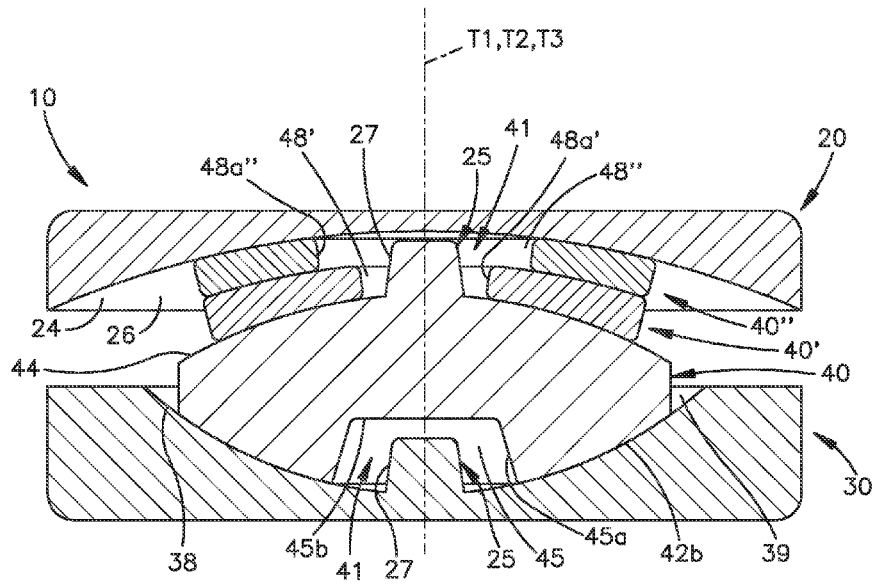
FIG. 4I is a sectional side elevation view of the intervertebral implant illustrated in FIG. 3I constructed in accordance with another alternative embodiment, in which the lower endplate includes a retainer pin, the lowermost insert includes a retainer pin and a retainer aperture, and the remaining inserts include retainer apertures.

Referring now to FIG. 4I, when the first pin 25 extending upwardly from the upper surface 42a of the body 42 of the insert 40 is received in the apertures 48' and 48" of the inserts 40' and 40", respectively, the inserts 40' and 40" are prevented from becoming dislodged from the implant 10 due to engagement between the inner surfaces 48a' and 48a" of the apertures 48' and 48" and the body 27 of the first pin 25. Furthermore, when the second pin 25 extending upwardly from the recess 38 of the lower endplate 30 is received in the aperture 45 defined in the lower surface 42b of the insert 40, the insert 40 is prevented from becoming dislodged from the implant 10 due to engagement between the inner surface 45a of the aperture 45 and the body 27 of the second pin 25. The first and second pins 25 can have any suitable lengths in the transverse direction such that they extend into the respective retainers 41 they compliment, such as the apertures 48' and 48", and the aperture 45, respectively, but do not contact the articulation surface 26 of the upper endplate 20 or the bottom surfaces 45b of the aperture 45. The pins 25 can have diameters that are less than the diameters of the respective apertures 48', 48", and 45 in which they are received. The pins 25 can further operate to limit the articulation, or motion between the inserts 40, 40', and 40" and the upper and lower endplates 20 and 30. For example, articulation is prevented when the inner surfaces 48a' and 48a" of the apertures 48' and 48" of the inserts 40' and 40" engages the body 27 of the first pin 25 extending upwardly from the upper surface 42a of the insert 40, and/or when the inner surface 45a of the aperture 45 of the insert 40 engages the body 27 of the second pin 25 extending upwardly from the recess 38 of the lower endplate 30. It should be appreciated that the diameters, or cross-sectional dimensions of the apertures 48', 48", and 45 can be sized the same or differently.

It should be appreciated that the components of the implant 10 can be constructed with any combination of the above-described retainers 41, as desired. For example, components of the implant 10 can be provided with one or more, up to a plurality of pins 25, one or more, up to a plurality of apertures, such as the apertures 23, 33, 45, and 48, and/or one or more, up to a plurality of rims 28 or 49. Furthermore, any combination of one or more, such as a plurality of retainers 41 can be defined on and/or in any individual component of the implant 10. It should further be appreciated that the retainers 41 can be provided the same or differently than illustrated and described herein. For example, the apertures 23, 33, 45, and 48 are not limited to the illustrated cylindrically shaped aperture geometries, and can alternatively be configured with any suitable aperture geometry. Moreover, the pin 25 is not limited to a body 27 with a uniform diameter, and can alternatively be provided with a tapered diameter that increases or decreases through one or more distinct portions of the body 27 in any combination. Additionally, the pin 25 is not limited to the illustrated cylindrically shaped body 27, and one or more, up to a plurality of pins 25 can be alternatively defined with any suitable body geometry. It should further be appreciated that the retainers 41 defined by the components of the implant 10 are not limited to the rims 28 and 49, the apertures 23, 33, 45, and 48, or the pin 25. For example, alternative retainers can include pivots, bolts, pins, grooves, channels, ridges, rings, or any other structures defined on and/or in any of the components of the implant 10. Of course, any or all such retainers can also be configured to limit articulation, or motion, between components of the implant 10.

The operation of the intervertebral implant 10 illustrated in FIGS. 2A-C, will now be described with reference to FIGS. 5A-B. In particular, the implant 10 is inserted into the intervertebral space 14 between adjacent vertebral bodies 12a-b, for example after a total discectomy has been performed, and is configured to restore anatomical movement of the vertebral bodies 12a-b. As illustrated, the upper bone-facing surface 22d of the upper endplate 20 is engaged with the superior vertebral surface 14a of the superior vertebral body 12a, and the lower bone-facing surface 32d of the lower endplate 30 is engaged with the inferior vertebral surface 14b of the inferior vertebral body 12b. The insert 40 is disposed in floating engagement between the upper and lower endplates 20 and 30.

Within a respective segment of a healthy spine, the intervertebral disc allows adjacent vertebral bodies to rotate, angulate, and/or translate (i.e., articulate) with respect to each other. For example, a superior vertebral body may articulate with respect to the adjacent inferior vertebral body about an instantaneous centre of rotation (ICR), or instantaneous centre in the inferior vertebral body during flexion and/or extension, such as the instantaneous centre PN illustrated in FIGS. 5A-B. It should be appreciated that the location of the instantaneous centre PN depicted in FIGS. 5A-B is not meant to be limiting, and that the location of the instantaneous centre within a particular vertebral body is dependent at least in part on the anatomy and the motion of the particular segment. The instantaneous centre PN can define an intangible, natural articulation surface AN having a generally spherical shape defined by the radius RN extending in a radially outward direction from the instantaneous centre PN, such that the natural articulation surface AN extends through the joint between the respective facets 16a and 16b of the adjacent vertebral bodies 12a and 12b.

In order to artificially mimic natural articulation using an intervertebral disc implant that defines a single articulation point requires precise alignment of the intervertebral disc implant within the intervertebral space. For example, if such an intervertebral disc implant and/or its components are anteriorly, posteriorly, and/or laterally misaligned within the intervertebral space, the artificial articulation surface created thereby is also misaligned, for example such that it does not correctly pass through the joints between the facets 16a and 16b. Such misalignment can cause movement of the respective motion segment (i.e., movement of the adjacent vertebral bodies 12a and 12b with respect to each other) to be detrimentally restricted. Restriction of motion segment movement can introduce undesirable stresses into, and/or cause undesirable contact between, the adjacent vertebral bodies, for example between the facets 16a and 16b of the adjacent vertebral bodies and/or their respective ligaments, thereby resulting in chronic or recurring pain for the patient and/or accelerated degeneration of the joint surfaces and/or bodies of the facets 16a and 16b.

Figure 5A:
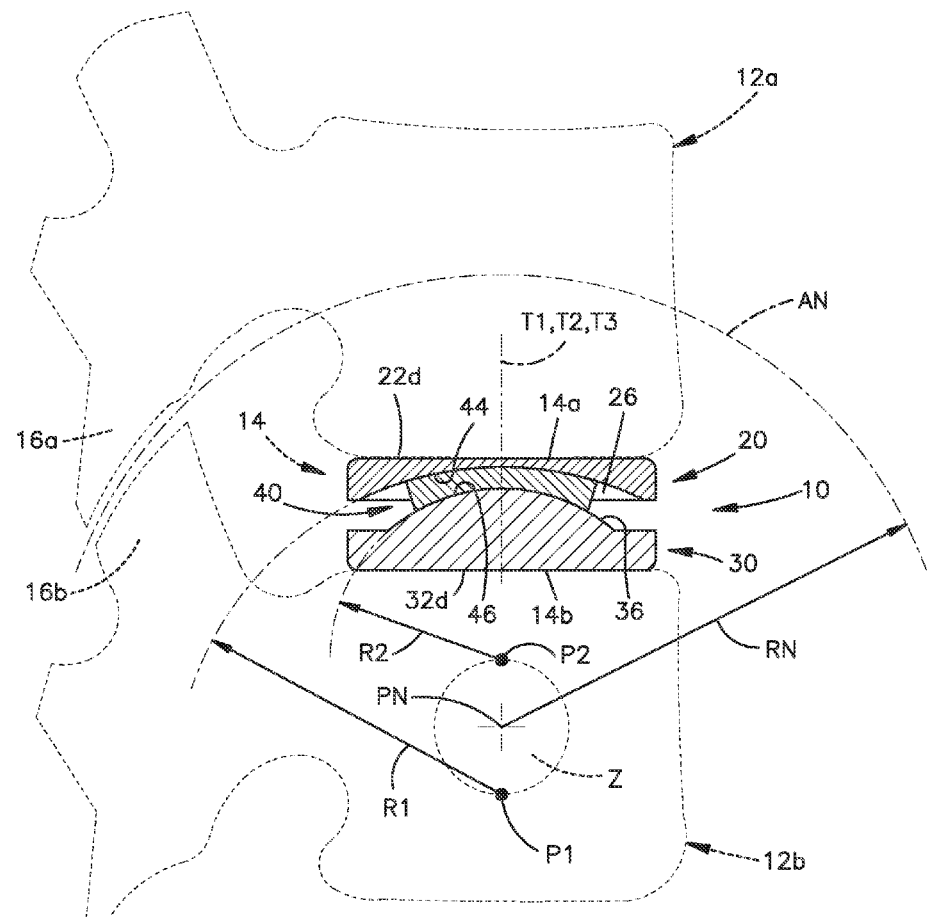
FIG. 5A is a sectional side elevation view of the intervertebral implant illustrated in FIG. 2A disposed in an intervertebral space between adjacent vertebral bodies.
Figure 5B:
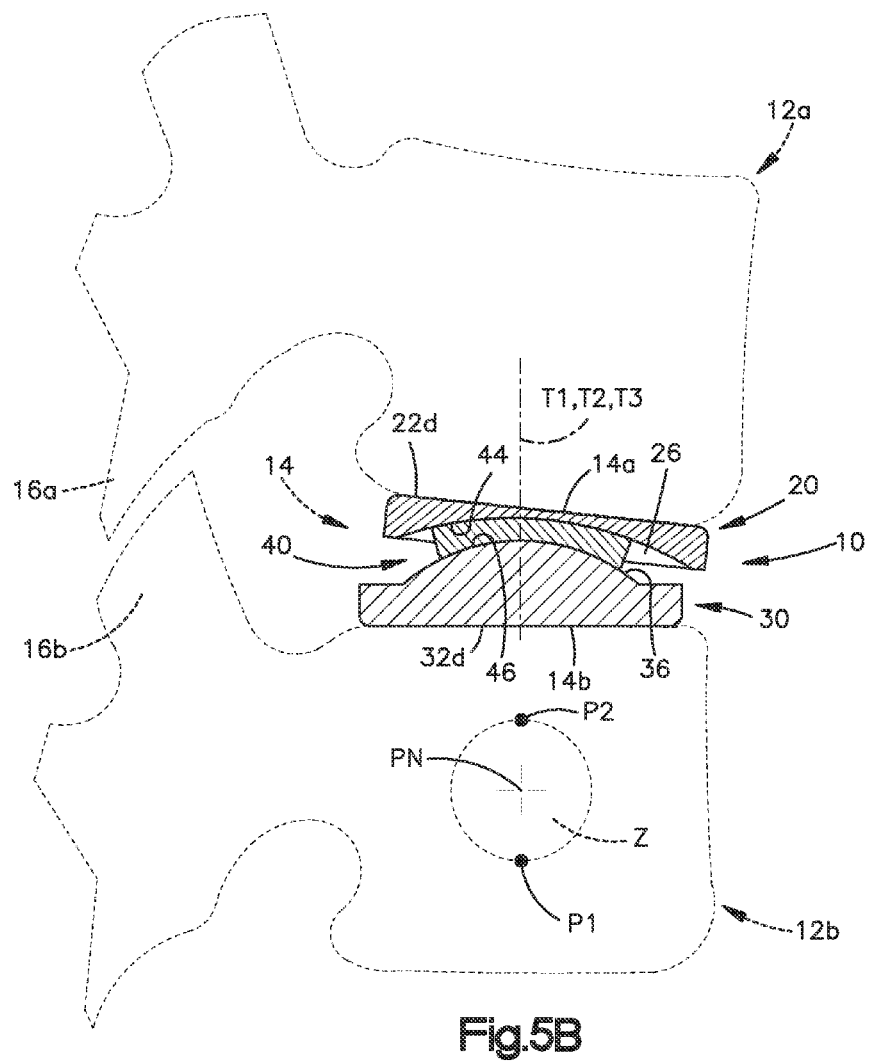
FIG. 5B is a sectional side elevation view of the intervertebral implant illustrated in FIG. 5A, showing the upper endplate articulated with respect to the implant insert along shared articulation surfaces therebetween, and the implant insert articulated with respect to the bottom endplate along shared articulation surfaces therebetween.

The intervertebral implant 10, as illustrated in FIGS. 5A-B, is constructed with an insert 40 that defines articulation surfaces 44 and 46 having first and second radii R1 and R2, respectively. The illustrated lengths of the radii R1 and R2 define two inferior articulation points P1 and P2 within the inferior vertebral body 12b. It should be appreciated that the articulation points P1 and/or P2 may be defined on transverse axes that are coincident, as illustrated, or non-coincident. It should further be appreciated that the radii R1 and/or R2 can be defined with shorter lengths such that the respective articulation points P1 and/or P2 are defined outside of the adjacent vertebral bodies, for example within the implant 10 itself. The articulation points P1 and P2 define an intangible articulation zone Z, having a generally spherical shape, within the inferior vertebral body 12b. When the implant 10 is assembled and disposed within the intervertebral space 14 between the adjacent vertebral bodies 12a and 12b such that the instantaneous centre PN is located within the articulation zone Z, movement of the adjacent vertebral bodies 12a and 12b with respect to each other (i.e., movement of the motion segment) will cause the components (e.g., the upper and lower endplates 20 and 30, the implant insert 40) of the implant 10 to articulate with respect to each other along one or more of the common, or shared, articulation surfaces 26 and 44, and 36 and 46. As described above, it should be appreciated that the articulation surfaces of one or more, up to all of the components of the implant 10 can be defined such that contact between adjacent components of the implant 10 along any of the respective shared, or common articulation surfaces is maintained throughout one or more portions of, up to the full range of articulation of the adjacent components with respect to each other. Maintaining surface contact along the articulation surfaces may reduce wear on the components of the implant 10.

The length and/or direction of the movement of the adjacent vertebral bodies 12a and 12b with respect to each other during normal anatomical function determines how the components of the implant 10 articulate with respect to each other along their respective articulation surfaces. For example, FIG. 5B depicts flexion of the spine, during which the superior vertebral body 12a rotates in a forward, or anterior, direction with respect to the inferior vertebral body 12b. As seen in FIG. 5B, the upper endplate 20 has articulated in an anterior direction with respect to the insert 40 along the shared articulation surfaces 26 and 44, and the insert 40 has articulated in an anterior direction with respect to the lower endplate 30 along the shared articulation surfaces 36 and 46. The combined articulations between the upper endplate 20 and the insert 40, and between the insert 40 and the lower endplate 30, allow the movement of the vertebral bodies 12a and 12b with respect to each other to mimic the natural articulation that would occur along the natural articulation surface AN prior to removal of the intervertebral disc. It should be appreciated that the introduction of additional articulation surfaces, for example by disposing one or more implant inserts 40 within the implant 10, may increase the articulation resolution of the implant 10, thereby allowing the implant 10 to more closely mimic the natural articulation that would occur along the natural articulation surface AN prior to removal of the intervertebral disc.

The articulation behavior of the components of the implant 10 with respect to each other can be determined by physical characteristics of the components. For example, the dimensions of the articulation zone Z, in particular its size, or volume, can determine how closely the implant 10 is able to mimic articulation along the natural articulation surface AN. The size of the articulation zone Z increases with increasing distance between the articulation points P1 and P2. Thus the selection of P1 and P2 will dictate the size of the articulation zone Z. As described above, when the articulation points of the implant 10 are configured such that the instantaneous centre PN is located within the articulation zone Z, articulation along one or more of the shared articulation surfaces of the components of the implant 10 acts to mimic natural articulation. Ensuring that the instantaneous centre PN is located within the articulation zone Z is at least partially dependent upon the size of the articulation zone Z and upon the accuracy with which the implant 10 is disposed within the intervertebral space 14. For example, a large articulation zone Z enables more latitude in placement of the implant 10. In other words, depending on the size of the articulation zone Z, a corresponding anterior, posterior, and/or lateral misalignment of the implant 10 can be accommodated, as long as the articulation zone Z is large enough to enclose the instantaneous centre PN when the implant 10 is in its inserted position.

The selection of P1 and P2 also determines the respective radii R1 and R2, that in turn define the curvature of the articulation surfaces 26 and 44, and 36 and 46. The degree of articulation between the components of the implant 10 can be determined by the difference in lengths of the first and second radii R1 and R2, respectively. For example, if the first radius R1 is substantially equal in length to the second radius R2, the components of the implant 10 may be more likely to articulate concurrently in response to movement of the vertebral bodies 12a and 12b with respect to each other. It is believed that a greater portion of the overall articulation of the implant will occur along the articulation surface(s) that correspond to the closest of the articulation points, such as P1 or P2, to the instantaneous centre PN.

The articulation behavior of the components of the implant 10 with respect to each other can also be determined by the material properties of the articulation surfaces. For example, materials exhibiting varying coefficients of friction can be selected for the construction of adjacent components of the implant. Additionally, one or more the articulation surfaces can be coated to induce varying coefficients of friction between the components of the implant 10.

It may be desirable to govern the articulation behavior along the articulation surfaces of the implant 10, such as the shared articulation surfaces 26 and 44, and/or 36 and 46, using one or more of the above-described techniques, for example to limit the amount of force that must be exerted on a particular component before that component will articulate with respect to an adjacent component. So governing the amount of force required to induce articulation may allow intrinsic limitation of articulation of the components of the implant 10 along one or more of the articulation surfaces 26 and 44, and/or 36 and 46. Intrinsically limiting the articulation of the components of the implant 10 may augment, or act as a substitution for, the above-described limitation of articulation by the retainers 41.

The operation of the intervertebral implant 10 illustrated in FIGS. 3G-I, will now be described with reference to FIGS. 6A-B. In particular, the implant 10 is inserted into the intervertebral space 14 between adjacent vertebral bodies 12a and 12b, for example after a total discectomy has been performed, and is configured to restore anatomical movement of the vertebral bodies 12a-b. As illustrated, the upper bone-facing surface 22d of the upper endplate 20 is engaged with the superior vertebral surface 14a of the superior vertebral body 12a, and the lower bone-facing surface 32d of the lower endplate 30 is engaged with the inferior vertebral surface 14b of the inferior vertebral body 12b. The inserts 40 and 40' are disposed in floating engagement between the upper and lower endplates 20 and 30.

Figure 6A:
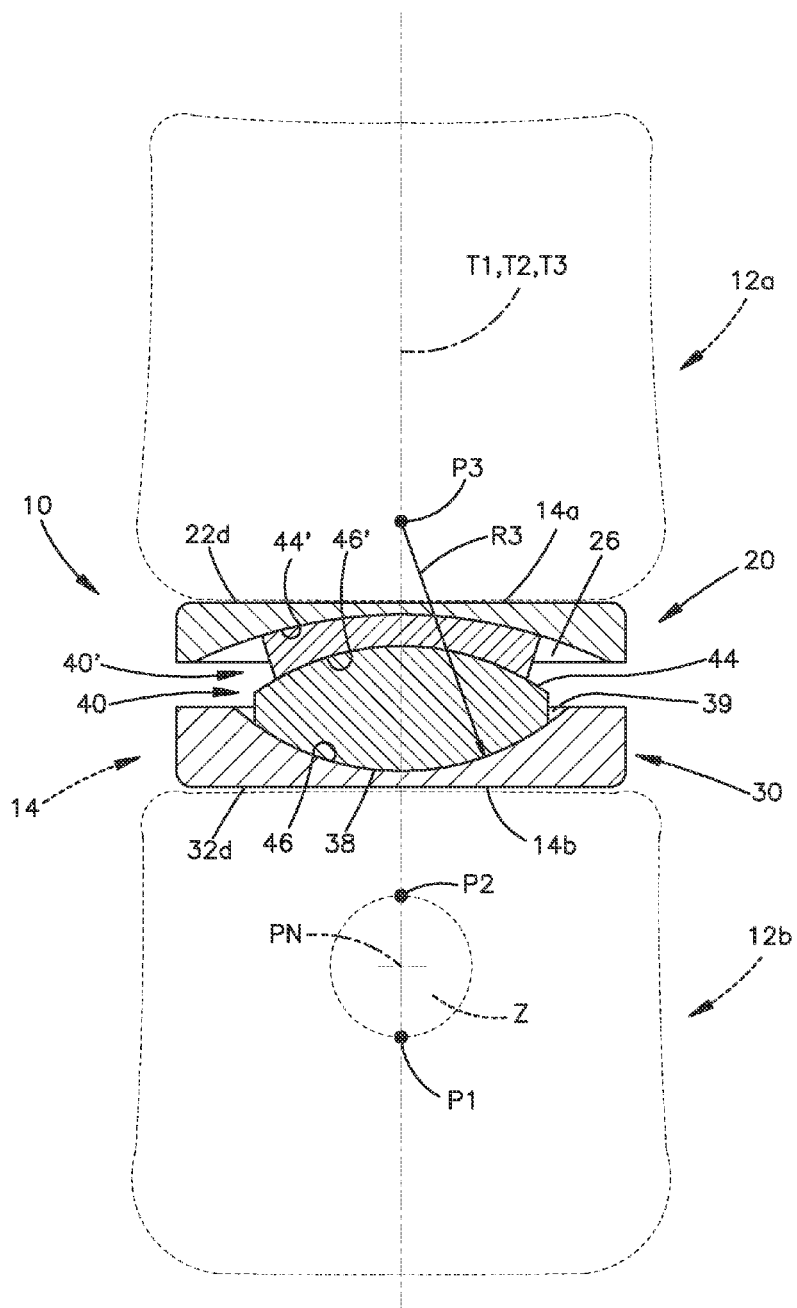
FIG. 6A is a sectional front elevation view of the intervertebral implant illustrated in FIG. 3I, disposed in an intervertebral space between adjacent vertebral bodies.
Figure 6B:
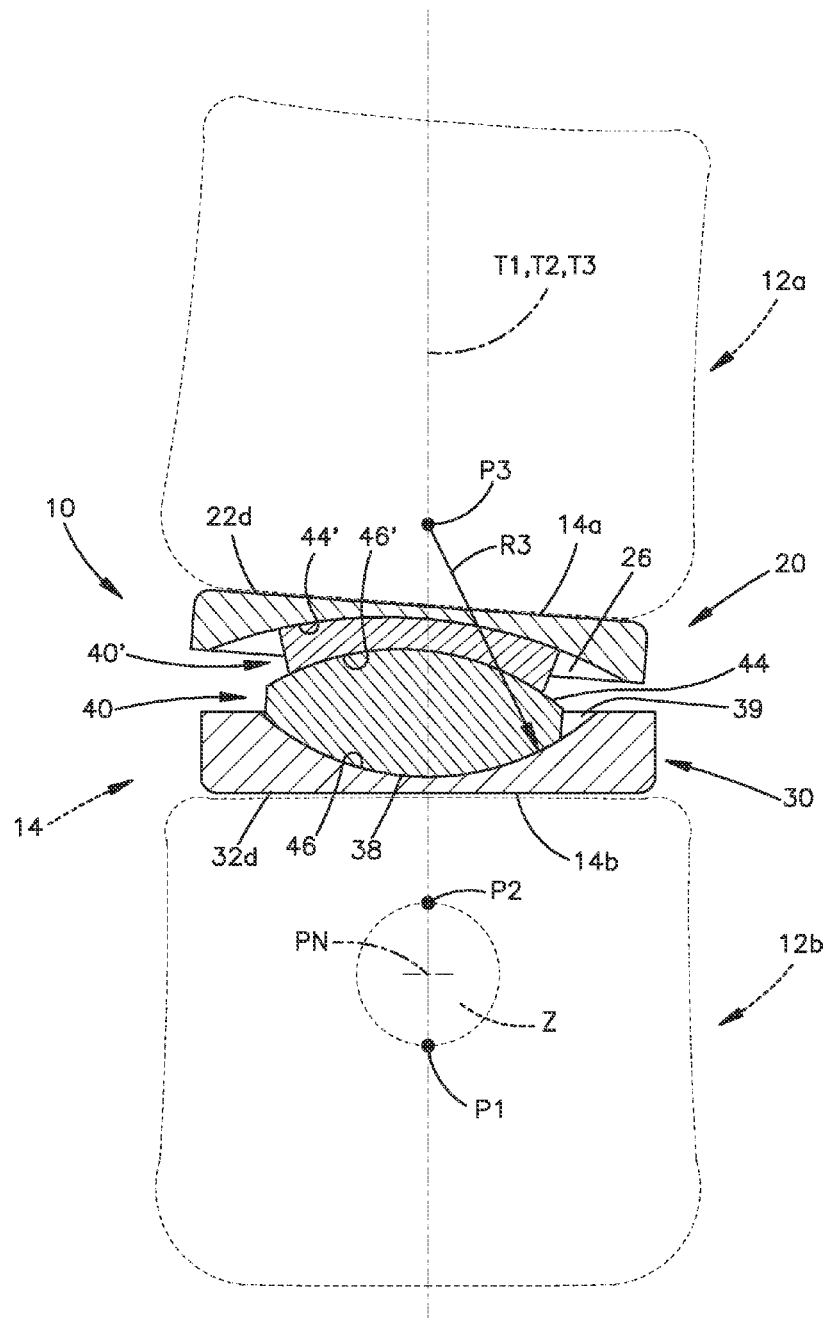
FIG. 6B is a sectional front elevation view of the intervertebral implant illustrated in FIG. 6A, showing the upper endplate and the implant inserts articulated with respect to the lower endplate along shared articulation surfaces between the lower implant insert and the bottom endplate.

The intervertebral implant 10, as illustrated in FIGS. 6A-B, is constructed with a pair of inserts 40 and 40'. The insert 40' defines the articulation surface 44' having a first radius R1. The inserts 40 and 40' defined common, or shared, articulation surfaces 44 and 46', respectively, having a second radius R2. The lengths of the radii R1 and R2 define the two inferior articulation points P1 and P2 within the inferior vertebral body 12b, and the corresponding articulation zone Z, as described above with respect to FIGS. 5A-B. The insert 40 also defines the articulation surface 46 having a third radius R3. The length of the radius R3 defines an articulation point P3 in the superior vertebral body 12a. It should be appreciated that the articulation points P1, P2 and/or P3 may be defined on transverse axes that are coincident, as illustrated, or non-coincident. It should further be appreciated that the radii R1, R2, and/or R3 can be defined with shorter lengths such that the respective articulation points P1, P2, and/or P3 are defined outside of the adjacent vertebral bodies, for example within the implant 10 itself. Articulation of the insert 40 with respect to the lower endplate 30 along the common, or shared, articulation surfaces 39 and 46, can enhance the ability of the implant 10 to mimic the natural articulation caused by motion segment movement (i.e., movement of the adjacent vertebral bodies 12a and 12b with respect to each other), in particular during lateral bending.

For example, FIG. 6B depicts lateral bending of the spine, during which the superior vertebral body 12a rotates in a side-to-side, or lateral, direction with respect to the inferior vertebral body 12b. As seen in FIG. 6B, the insert 40 has articulated with respect to the lower endplate 30 along the shared articulation surfaces 46 and 39, in a direction generally opposing the lateral rotation of the superior vertebral body 12a with respect to the inferior vertebral body 12b. As illustrated, the upper endplate 20, the insert 40', and the insert 40, have articulated with respect to the lower endplate 30 in unison, that is, they have remained in a static position with respect to each other, as the insert 40 articulated with respect to the lower endplate 30 along the shared articulation surfaces 46 and 39. Of course, as described above, any number of, or all of, the upper and lower endplates 20 and 30, and the inserts 40 and 40', are capable of concurrently articulating with respect to each other along the respective shared articulation surfaces, for example during combined motion segment movements, such as lateral bending in conjunction with flexion or extension. Further, as described above, it should be appreciated that the articulation surfaces of one or more, up to all of the components of the implant 10 can be defined such that contact between adjacent components of the implant 10 along any of the respective shared, or common articulation surfaces is maintained throughout one or more portions of, up to the full range of articulation of the adjacent components with respect to each other. Maintaining surface contact along the articulation surfaces may reduce wear on the components of the implant 10.

It should be appreciated that additional articulation surfaces defining respective additional superior articulation points could be introduced, for example by disposing one or more additional implant inserts 40 between the articulation surfaces 46 and 39. Such additional superior articulation points may define a superior articulation zone in the superior vertebral body 12a. It should further be appreciated that providing additional articulation surfaces may increase the articulation resolution of the implant 10, thereby allowing the implant 10 to more closely mimic the natural articulations that would occur within the motion segment prior to removal of the intervertebral disc.

During insertion into the intervertebral space 14, the implant 10 is aligned with the intervertebral space 14. The vertebral bodies 12a and 12b are retracted such that the anterior ends of the vertebral bodies 12a and 12b exhibit a greater separation in the cranial-caudal direction than the posterior ends of the vertebral bodies 12a and 12b. Thus, the intervertebral space 14 defines a cranial-caudal dimension at the anterior end that is greater than the caudal-cranial dimension of the intervertebral space 14 at the posterior end. The implant 10 is inserted into the intervertebral space 14, and the upper and lower endplates 20 and 30 are secured to the respective superior and inferior vertebral surfaces 14a and 14b of the vertebral bodies 12a and 12b, respectively, as appropriate. The implant 10 can be inserted in an assembled configuration, or the individual components of the implant 10 can be assembled within the intervertebral space 14 as part of the insertion process. The individual components included in the implant 10 can be selected and/or positioned by a surgeon, for example based on the region of the spine into which the implant 10 is to be inserted, particular patient anatomy, and the like. Alternatively, component selection and/or placement location of the implant 10 can be at least partially, up to totally determined with the use of a selection tool, such as an imaging apparatus coupled to a software-based utility configured to analyze a patient's anatomy and select an optimal configuration for the implant 10.

It should be appreciated that the intervertebral implant with multiple radii 10 can be constructed with any dimensions desirable for implantation into any intervertebral space within the spine. Furthermore, while the intervertebral implant 10 as illustrated and described herein is configured as a total disc replacement device, implants constructed in accordance with the teachings described herein are readily configurable for use with a range of bone-anchored orthopedic prostheses, such as interbody spacers, hip and knee replacement implants, and the like.

It should further be appreciated that a variety of intervertebral implant kits can be created and/or provided that include one or more components of the intervertebral implant with multiple radii 10. The components of the kits may be configured the same or differently. For example, a single kit might include one or more upper and/or lower endplates 20 and/or 30 having recesses and/or projections defining varying surface geometries, one or more implant inserts 40 of varying configurations and/or sizes, and so on, depending, for example, on the location within the spine where the implant will be inserted, the anatomy of the particular patient, and the like. The kits may also be configured differently with respect to which components of the intervertebral implant 10 are included in the kits. For example, a single kit might include a plurality of upper endplates 20 having recesses and/or projections of varying surface geometries, a plurality of lower endplates 30 having recesses and/or projections of varying surface geometries, or a plurality of implant inserts 40 of varying configurations and/or sizes, and so on.

Although the components of the intervertebral implant with multiple radii 10 have been described herein with reference to preferred embodiments and/or preferred methods, it should be understood that the words which have been used herein are words of description and illustration, rather than words of limitation. For example, it should be appreciated that the upper and/or lower endplates 20 and 30, respectively, may be defined with any combination of projections and/or recesses as desired, that the projections and/or recesses can have any combination of spherical, compound radii, or any other curved, or non-curved, surface geometry as desired, and that the upper and/or lower endplates 20 and 30 can be configured to floatingly engage with any number of implant inserts 40 having any combination of geometric configuration and/or sizes as desired. Furthermore, it should be appreciated that although the intervertebral implant with multiple radii 10 has been described herein with reference to particular structure, methods, and/or embodiments, the scope of the instant disclosure is not intended to be limited to those particulars, but rather is meant to extend to all structures, methods, and/or uses of the intervertebral implant with multiple radii 10. Those skilled in the relevant art, having the benefit of the teachings of this specification, may effect numerous modifications to the intervertebral implant with multiple radii 10 as described herein, and changes may be made without departing from the scope and spirit of the instant disclosure, for instance as recited in the appended claims.

What is claimed:

1. An implant configured to be disposed in an intervertebral space between an inferior vertebral body and an adjacent superior vertebral body, the implant comprising:
   an upper implant body having an outer bone-facing surface configured to engage the superior vertebral body, the upper implant body having an opposed inner articulation surface that has a first curvature along a first direction and a second curvature along a second direction that is substantially perpendicular to the first direction where the first curvature has a different degree of curvature than the second curvature;
   a lower implant body having an outer bone-facing surface configured to engage the inferior vertebral body, the lower implant body having an opposed second inner articulation surface that has a third curvature along the first direction and a fourth curvature along the second direction where the third curvature has a different degree of curvature than the fourth curvature; and
   an insert assembly disposed between the upper and lower implant bodies, the insert assembly having an upper articulation surface and a lower articulation surface, the upper articulation surface having the same surface geometry as the inner articulation surface of the upper implant body, and the lower articulation surface having the same surface geometry as the inner articulation surface of the lower implant body,
   wherein the first curvature and third curvature are different and wherein the second curvature and fourth curvature are different,
   wherein the first curvature is defined by a radius of a first articulation point, the second curvature is defined by a radius of a second articulation point, and at least one of the upper and lower articulation surfaces of the implant assembly is defined by a radius of a third articulation point,
   wherein at least one of the first, second, and third articulation points is configured to be located outside the inferior vertebral body when the implant is disposed in the intervertebral space.

2. The implant as recited in claim 1, wherein when the implant is articulated, surface contact between at least one of the upper implant body and the insert assembly or the lower implant body and the insert assembly is maintained throughout a range of articulation along the first curvature.

3. The implant as recited in claim 1, wherein the inner articulation surfaces of both the upper and lower implant bodies are concave surfaces.

4. The implant as recited in claim 1, wherein the insert assembly comprises one insert, the one insert having an insert body that extends between the inner articulation surfaces of the upper and lower implant bodies.

5. The implant as recited in claim 4, wherein the insert body has an aperture defined therein.

6. The implant as recited in claim 5, wherein the aperture extends through the insert body from the upper curved surface through the lower curved surface.

7. The implant as recited in claim 1, wherein the inner articulation surfaces of both the upper and lower implant bodies are convex.

8. The implant as recited in claim 1, wherein at least one of the inner articulation surfaces of the upper and lower implant bodies defines a retainer.

9. The implant as recited in claim 8, wherein the retainer is a pin extending outward from the at least inner articulation surfaces of the upper and lower implant bodies.

10. The implant as recited in claim 8, wherein the retainer is a rim extending along an inner rim surface defined between the at least one of the inner articulation surfaces of the upper and lower implant bodies.

11. The implant as recited in claim 10, wherein the insert assembly comprises one insert, the one insert having a round insert body that extends between the upper and lower inner articulation surfaces of the upper and lower implant bodies, and
   wherein the insert body has a peripheral surface configured to engage with the rim.

12. The implant as recited in claim 8, wherein the retainer is an aperture extending into the at least one of the upper and lower surfaces.

13. The implant as recited in claim 1, wherein the insert assembly comprises a plurality of inserts, each insert of the plurality of inserts having a respective round insert body that extends between respective inner articulation surfaces of the upper and lower implant bodies.

14. The implant as recited in claim 1, wherein the insert assembly comprises a plurality of inserts, each insert of the plurality of inserts having a respective round insert body that extends between respective inner articulation surfaces of the upper and lower implant bodies.

15. An implant configured to be disposed in an intervertebral space between a superior vertebral body and an adjacent inferior vertebral body, the implant comprising:
    an upper implant body having an outer bone-facing surface configured to engage the superior vertebral body, the upper implant body having an opposed inner articulation surface that has a first curvature along a first direction and a second curvature along a second direction that is substantially perpendicular to the first direction where the first curvature has a different degree of curvature than the second curvature;
    a lower implant body having an outer bone-facing surface configured to engage the inferior vertebral body, the lower implant body having an opposed inner articulation surface that has a third curvature along the first direction and a fourth curvature along the second direction where the third curvature has a different degree of curvature than the fourth curvature; and
    an insert assembly disposed between the upper and lower implant bodies, the insert assembly having an upper articulation surface and a lower articulation surface, the upper articulation surface having the same surface geometry as the inner articulation surface of the upper implant body, and the lower articulation surface having the same surface geometry as the inner articulation surface of the lower implant body,
    wherein the first curvature and third curvature are different and wherein the second curvature and fourth curvature are different,
    wherein the first curvature is defined by a radius of a first articulation point and the second curvature is defined by a radius of a second articulation point, and at least one of the first and second articulation points is configured to be located outside the inferior vertebral body when the implant is disposed in the intervertebral space.

16. The implant as recited in claim 15, wherein at least one of the upper and lower articulation surfaces of the insert assembly is defined by a radius of a third articulation point.

17. The implant as recited in claim 16, wherein the third articulation point is configured to be located in the inferior vertebral body when the implant is disposed in the intervertebral space.

18. The implant as recited in claim 16, wherein the third articulation point is configured to be located outside the inferior vertebral body when the implant is disposed in the intervertebral space.

19. The implant as recited in claim 15, wherein when at least one of the upper implant body or the insert assembly are articulated with respect to the other, surface contact between the upper implant body and the insert assembly along the first curvature is maintained throughout a range of articulation along the first curvature.

20. The implant as recited in claim 15, wherein when at least one of the lower implant body or the insert assembly are articulated with respect to the other, surface contact between the lower implant body and the insert assembly along the second articulation surface is maintained throughout a range of articulation along the second articulation surface.

21. The implant as recited in claim 15, wherein the first curvature is defined by a radius of a first articulation point and the second curvature is defined by a radius of a second articulation point, and the radii of the first and second articulation points have different lengths.

22. The implant as recited in claim 15, wherein inner articulation surfaces of both the upper and lower implant bodies are concave surfaces.

23. The implant as recited in claim 15, wherein the inner articulation surfaces of both the upper and lower implant bodies are convex.

24. The implant as recited in claim 15 wherein the insert assembly comprises one insert, the one insert having an insert body that extends between the inner articulation surfaces of the upper and lower implant bodies.

25. The implant as recited in claim 24, wherein the insert body has an aperture defined therein.

26. The implant as recited in claim 25, wherein the aperture extends through the insert body from the upper curved surface through the lower curved surface.

27. The implant as recited in claim 15, wherein at least one of the inner articulation surfaces of the upper and lower implant bodies defines a retainer.

28. The implant as recited in claim 27, wherein the retainer is a pin extending outward from the at least inner articulation surfaces of the upper and lower implant bodies.

* * * * *